US006297197B1

(12) United States Patent
Fields et al.

(10) Patent No.: US 6,297,197 B1
(45) Date of Patent: Oct. 2, 2001

(54) 4-AMINOPICOLINATES AND THEIR USE AS HERBICIDES

(75) Inventors: Stephen Craig Fields; Anita Lenora Alexander, both of Indianapolis; Terry William Balko, Greenfield; Leslie Anne Bjelk, Indianapolis; Ann Marie Buysse; Renee Joan Keese, both of Carmel, all of IN (US); Karl Leopold Krumel, Midland, MI (US); William Chi-Leung Lo; Christian Thomas Lowe, both of Indianapolis, IN (US); John Sanders Richburg, III, Westfield; James Melvin Ruiz, Zionsville, both of IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/760,111

(22) Filed: Jan. 12, 2001

Related U.S. Application Data

(60) Provisional application No. 60/176,720, filed on Jan. 14, 2000.

(51) Int. Cl.[7] ......................... C07D 213/79; A01N 43/40

(52) U.S. Cl. .......................... 504/260; 504/244; 504/255; 546/296; 546/297; 546/306; 546/311; 546/312

(58) Field of Search .................................... 546/306, 311, 546/312, 296, 297; 504/255, 260, 244

(56) References Cited

U.S. PATENT DOCUMENTS

| | | | |
|---|---|---|---|
| 3,234,229 | 2/1966 | Redemann | 260/296 |
| 3,285,925 | 11/1966 | Johnston et al. | 260/294.9 |
| 3,317,549 | 5/1967 | Johnston et al. | 260/294.9 |
| 3,325,272 | 6/1967 | Hamaker et al. | 71/2.5 |
| 3,334,108 | 8/1967 | Johnston et al. | 260/294.8 |
| 3,755,338 | 8/1973 | Gulbenk | 260/295 |

FOREIGN PATENT DOCUMENTS 788756 3/1973 (BE) .

OTHER PUBLICATIONS

K. Ramanad, et al., pp. 2251–2256, vol. 59, No. 7, Jul. 1993, *Applied and Environmental Microbiology.*

*Primary Examiner*—Zinna Northington Davis
(74) *Attorney, Agent, or Firm*—Craig E. Mixan

(57) ABSTRACT

4-Aminopicolinic acids, having halogen, alkoxy, alkylthio, aryloxy, heteroaryloxy or trifluoromethyl substituents in the 3-, 5- and 6-positions, and their amine and acid derivatives are potent herbicides demonstrating a broad spectrum of weed control.

14 Claims, No Drawings

4-AMINOPICOLINATES AND THEIR USE AS HERBICIDES

This application claims priority to provisional application 60/176,720 filed Jan. 14, 2000.

BACKGROUND OF THE INVENTION

This invention relates to certain novel 4-aminopicolinates and their derivatives and to the use of these compounds as herbicides.

A number of picolinic acids and their pesticidal properties have been described in the art. For example, U.S. Pat. No. 3,285,925 discloses 4-amino-3,5,6-trichloropicolinic acid derivatives and their use as plant growth control agents and herbicides. U.S. Pat. No. 3,325,272 discloses 4-amino-3,5-dichloropicolinic acid derivatives and their use for the control of plant growth. U.S. Pat. No. 3,317,549 discloses 3,6-dichloropicolinic acid derivatives and their use as plant growth control agents. U.S. Patent 3,334,108 discloses chlorinated dithiopicolinic acid derivatives and their use as parasiticides. U.S. Pat. No. 3,234,229 discloses 4-amino-polychloro-2-trichloromethylpyridines and their use as herbicides. In *Applied and Environmental Microbiology*, Vol. 59, No. 7, July 1993, pp. 2251–2256, 4-amino-3,6-dichloropicolinic acid is identified as a product of the anaerobic degradation of 4-amino-3,5,6-trichloropicolinic acid, the commercially available herbicide picloram.

While picloram is recommended for the control of woody plants and broadleaf weeds in certain applications, its properties are not ideal. It would be highly desirable to discover related compounds that are more potent, more selective or of broader spectrum in their herbicidal activity and/or that have improved toxicological or environmental properties.

SUMMARY OF THE INVENTION

It has now been found that certain 4-aminopicolinic acids and their derivatives having selected substituents in the 3-, 5-, and 6-positions are potent herbicides with a broad spectrum of weed control and excellent crop selectivity. The compounds further possess excellent toxicological or environmental profiles.

The invention includes compounds of Formula I:

I

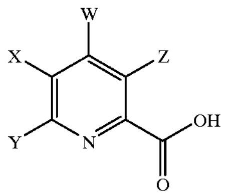

wherein

X represents H, halogen, $C_1$–$C_6$ alkoxy, $C_1$–$C_6$ alkylthio, aryloxy, nitro or trifluoromethyl;

Y represents halogen, $C_1$–$C_6$ alkoxy, $C_1$–$C_6$ alkylthio, aryloxy, heteroaryloxy or trifluoromethyl;

Z represents halogen, $C_1$–$C_6$ alkoxy, $C_1$–$C_6$ alkylthio, aryloxy or nitro; and W represents —$NO_2$, —$N_3$, —$NR_1R_2$, —N═$CR_3R_4$ or —NHN═$CR_3R_4$ where $R_1$ and $R_2$ independently represent H, $C_1$–$C_6$ alkyl, $C_3$–$C_6$ alkenyl, $C_3$–$C_6$ alkynyl, aryl, heteroaryl, hydroxy, $C_1$–$C_6$ alkoxy, amino, $C_1$–$C_6$ acyl, $C_1$–$C_6$ carboalkoxy, $C_1$–$C_6$ alkylcarbamyl, $C_1$–$C_6$ alkylsulfonyl, $C_1$–$C_6$ trialkylsilyl or $C_1$–$C_6$ dialkyl phosphonyl or $R_1$ and $R_2$ taken together with N represent a 5- or 6-membered saturated or unsaturated ring which may contain additional O, S or N heteroatoms; and $R_3$ and $R_4$ independently represent H, $C_1$–$C_6$ alkyl, $C_3$–$C_6$ alkenyl, $C_3$–$C_6$ alkynyl, aryl or heteroaryl or $R_3$ and $R_4$ taken together with ═C represent a 5- or 6-membered saturated ring; and agriculturally acceptable derivatives of the carboxylic acid, with the proviso that when X represents H or Cl, then Y and Z are not both Cl.

Compounds of Formula I wherein X represents H or F, wherein Y represents F, Cl, Br or aryloxy, wherein Z represents Cl and wherein $R_1$ and $R_2$ represent H are independently preferred.

The invention includes herbicidal compositions comprising a herbicidally effective amount of a 4-amino-picolinate of Formula I:

I

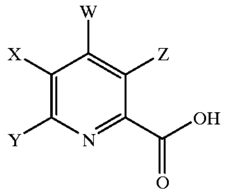

wherein

X represents H, halogen, $C_1$–$C_6$ alkoxy, $C_1$–$C_6$ alkylthio, aryloxy, nitro or trifluoromethyl;

Y represents halogen, $C_1$–$C_6$ alkoxy, $C_1$–$C_6$ alkylthio, aryloxy, heteroaryloxy or trifluoromethyl;

Z represents halogen, $C_1$–$C_6$ alkoxy, $C_1$–$C_6$ alkylthio, aryloxy or nitro; and W represents —$NO_2$, —$N_3$, —$NR_1R_2$, —N═$CR_3R_4$ or —NHN═$CR_3R_4$ where $R_1$ and $R_2$ independently represent H, $C_1$–$C_6$ alkyl, $C_3$–$C_6$ alkenyl, $C_3$–$C_6$ alkynyl, aryl, heteroaryl, hydroxy, $C_1$–$C_6$ alkoxy, amino, $C_1$–$C_6$ acyl, $C_1$–$C_6$ carboalkoxy, $C_1$–$C_6$ alkylcarbamyl, $C_1$–$C_6$ alkylsulfonyl, $C_1$–$C_6$ trialkylsilyl or $C_1$–$C_6$ dialkyl phosphonyl or $R_1$ and $R_2$ taken together with N represent a 5- or 6-membered saturated or unsaturated ring which may contain additional O, S or N heteroatoms; and $R_3$ and $R_4$ independently represent H, $C_1$–$C_6$ alkyl, $C_3$–$C_6$ alkenyl, $C_3$–$C_6$ alkynyl, aryl or heteroaryl or $R_3$ and $R_4$ taken together with =C represent a 5- or 6-membered saturated ring; and agriculturally acceptable derivatives of the carboxylic acid, with the proviso that when X represents Cl, then Y and Z are not both Cl in admixture with an agriculturally acceptable adjuvant or carrier. The invention also includes a method of use of the compounds and compositions of the present invention to kill or control undesirable vegetation by application of an herbicidal amount of the compound to the vegetation or to the locus of the vegetation as well as to the soil prior to emergence of the vegetation. The use of the compounds to kill or control woody plants and broadleaf weeds in grass crops is a preferred utility and post-emergent application of the compounds to the undesirable vegetation is a preferred method of application.

DETAILED DESCRIPTION OF THE INVENTION

The herbicidal compounds of the present invention are derivatives of 4-aminopicolinic acids:

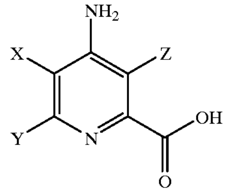

These compounds are characterized by possessing halogen, $C_1$–$C_6$ alkoxy, $C_1$–$C_6$ alkylthio, aryloxy or nitro substituents in the 3-position with halogen being preferred and chlorine being most preferred; by possessing hydrogen, halogen, $C_1$–$C_6$ alkoxy, $C_1$–$C_6$ alkylthio, aryloxy, nitro or trifluoromethyl substituents in the 5-position with hydrogen and fluorine being preferred; and by possessing halogen, $C_1$–$C_6$ alkoxy, $C_1$–$C_6$ alkylthio, aryloxy, heteroaryloxy or trifluoromethyl substituents in the 6-position with fluorine, chlorine, bromine or aryloxy being preferred. Preferred aryloxy groups in the 6-position are 3-substituted phenoxy groups, most preferably phenoxy groups substituted with halogen or $C_1$–$C_4$ alkyl groups in the 3-position.

The amino group at the 4-position can be unsubstituted or substituted with one or more $C_1$–$C_6$ alkyl, $C_3$–$C_6$ alkenyl, $C_3$–$C_6$ alkynyl, aryl, heteroaryl, hydroxy, $C_1$–$C_6$ alkoxy or amino substituents. The amino group can be further derivatized as an amide, a carbamate, a urea, a sulfonamide, a silylamine, a phosphoramidate, an imine or a hydrazone. Such derivatives are capable of breaking down into the amine. An unsubstituted amino group or one substituted with one or more alkyl substituents is preferred.

The carboxylic acids of Formula I are believed to be the compounds that actually kill or control undesirable vegetation and are typically preferred. Analogs of these compounds in which the acid or amine group of the picolinic acid is derivatized to form a related substituent that can be transformed within plants or the environment to a acid group possess essentially the same herbicidal effect and are within the scope of the invention. Therefore, an "agriculturally acceptable derivative", when used to describe the carboxylic acid functionality at the 2-position, is defined as any salt, ester, acylhydrazide, imidate, thioimidate, amidine, amide, orthoester, acylcyanide, acyl halide, thioester, thioester, dithiolester, nitrile or any other acid derivative well known in the art which (a) does not substantially affect the herbicidal activity of the active ingredient, i.e., the 4-aminopicolinic acid, and (b) is or can be hydrolyzed in plants or soil to the picolinic acid of Formula I that, depending upon the pH, is in the dissociated or the undissociated form. Likewise, an "agriculturally acceptable derivative", when used to describe the amine functionality at the 4-position, is defined as any salt, silylamine, phosphorylamine, phosphinimine, phosphoramidate, sulfonamide, sulfinimine, sulfoximine, aminal, hemiaminal, amide, thioamide, carbamate, thiocarbamate, amidine, urea, imine, nitro, nitroso, azide, or any other nitrogen containing derivative well known in the art which (a) does not substantially affect the herbicidal activity of the active ingredient, i.e., the 4-aminopicolinic acid, and (b) is or can be hydrolyzed in plants or soil to a free amine of Formula I. N-Oxides which are also capable of breaking into the parent pyridine of Formula I are also covered by the scope of this invention.

Suitable salts include those derived from alkali or alkaline earth metals and those derived from ammonia and amines. Preferred cations include sodium, potassium, magnesium, and aminium cations of the formula:

$$R_5R_6R_7NH^+$$

wherein $R_5$, $R_6$, and $R_7$ each, independently represents hydrogen or $C_1$–$C_{12}$ alkyl, $C_3$–$C_{12}$ alkenyl or $C_3$–$C_{12}$ alkynyl, each of which is optionally substituted by one or more hydroxy, $C_1$–$C_4$ alkoxy, $C_1$–$C_4$ alkylthio or phenyl groups, provided that $R_5$, $R_6$, and $R_7$ are sterically compatible. Additionally, any two of $R_5$, $R_6$, and $R_7$ together may represent an aliphatic difunctional moiety containing 1 to 12 carbon atoms and up to two oxygen or sulfur atoms. Salts of the compounds of Formula I can be prepared by treatment of compounds of Formula I with a metal hydroxide, such as sodium hydroxide, or an amine, such as ammonia, trimethylamine, diethanolamine, 2-methyl-thiopropylamine, bisallylamine, 2-butoxyethylamine, morpholine, cyclododecylamine, or benzylamine. Amine salts are often preferred forms of the compounds of Formula I because they are water-soluble and lend themselves to the preparation of desirable aqueous based herbicidal compositions.

Suitable esters include those derived from $C_1$–$C_{12}$ alkyl, $C_3$–$C_{12}$ alkenyl or $C_3$–$C_{12}$ alkynyl alcohols, such as methanol, iso-propanol, butanol, 2-ethylhexanol, butoxyethanol, methoxypropanol, allyl alcohol, propargyl alcohol or cyclohexanol. Esters can be prepared by coupling of the picolinic acid with the alcohol using any number of suitable activating agents such as those used for peptide couplings such as dicyclohexylcarbodiimide (DCC) or carbonyl diimidazole (CDI), by reacting the corresponding acid chloride of a picolinic acid of Formula I with an appropriate alcohol or by reacting the corresponding picolinic acid of Formula I with an appropriate alcohol in the presence of an acid catalyst. Suitable amides include those derived from ammonia or from $C_1$–$C_{12}$ alkyl, $C_3$–$C_{12}$ alkenyl or $C_3$–$C_{12}$ alkynyl mono- or di-substituted amines, such as but not limited to dimethylamine, diethanolamine, 2-methylthiopropylamine, bisallylamine, 2-butoxyethylamine, cyclododecylamine, benzylamine or cyclic or aromatic amines with or without additional heteroatoms such as but not limited to aziridine, azetidine, pyrrolidine, pyrrole, imidazole, tetrazole or morpholine. Amides can be prepared by reacting the corresponding picolinic acid chloride, mixed anhydride, or carboxylic ester of Formula I with ammonia or an appropriate amine.

The terms "alkyl", "alkenyl" and "alkynyl", as well as derivative terms such as "alkoxy", "acyl", "alkylthio" and "alkylsulfonyl", as used herein, include within their scope straight chain, branched chain and cyclic moieties. Unless specifically stated otherwise, each may be unsubstituted or substituted with one or more substituents selected from but not limited to halogen, hydroxy, alkoxy, alkylthio, $C_{1-C6}$ acyl, formyl, cyano, aryloxy or aryl, provided that the substituents are sterically compatible and the rules of chemical bonding and strain energy are satisfied. The terms "alkenyl" and "alkynyl" are intended to include one or more unsaturated bonds.

The term "aryl", as well as derivative terms such as "aryloxy", refers to a phenyl or naphthyl group. The term "heteroaryl", as well as derivative terms such as "heteroaryloxy", refers to a 5- or 6-membered aromatic ring containing one or more heteroatoms, viz., N, O or S; these heteroaromatic rings may be fused to other aromatic systems. The aryl or heteroaryl substituents may be unsubstituted or substituted with one or more substituents selected from halogen, hydroxy, nitro, cyano, aryloxy, formyl, $C_1$–$C_6$ alkyl, $C_2$–$C_6$ alkenyl, $C_2$–$C_6$ alkynyl, $C_1$–$C_6$ alkoxy, halogenated $C_1$–$C_6$ alkyl, halogenated $C_1$–$C_6$ alkoxy, $C_1$–$C_6$ acyl, $C_1$–$C_6$ alkylthio, $C_l$–$C_6$ alkylsulfinyl, $C_1$–$C_6$ alkylsulfonyl, aryl, $C_1$–$C_6$OC(O)alkyl, $C_1$–$C_6$ NHC(O) alkyl, C(O)OH, $C_1$–$C_6$C(O)Oalkyl, C(O)$NH_2$, $C_1$–$C_6$ C(O) NHalkyl, or $C_1$–$C_6$C(O)N(alkyl)2, provided that the substituents are sterically compatible and the rules of chemical bonding and strain energy are satisfied.

Unless specifically limited otherwise, the term halogen includes fluorine, chlorine, bromine, and iodine.

The compounds of Formula I can be made using well-known chemical procedures. The required starting materials are commercially available or readily synthesized utilizing standard procedures.

In general, reduction of picolinate N-oxides can be used to prepare the corresponding picolinates. Electrolytic dehalogenation of 5-halogenated picolinates can be used to prepare the 5-H (unsubstituted) picolinates, and hydrolysis of pyridines substituted at the 2 position by nitriles, amides, esters and other hydrolyzable functionalities can be used to prepare the desired picolinates.

4-N-amide, carbamate, urea, sulfonamide, silylamine and phosphoramidate amino derivatives can be prepared by the reaction of the free amino compound with, for example, a suitable acid halide, chloroformate, carbamyl chloride, sulfonyl chloride, silyl chloride or chlorophosphate. The imine or hydrazone can be prepared by reaction of the free amine or hydrazine with a suitable aldehyde or ketone.

6-Bromo analogs can be prepared by the reduction of several key intermediates, e.g., the corresponding 6-bromo-4-azido, 6-bromo-4-nitro, and 6-bromo-4-nitro pyridine N-oxide analogs. These intermediates, in turn, can be prepared either by nucleophilic displacement of 6-bromo-4-halo analogs with $NaN_3$ or by electrophilic nitration of the corresponding 6-bromopyridine-N-oxides. Alternatively, such analogs can be prepared by direct amination of the corresponding 4,6-dibromo analogs.

6-Fluoro analogs can be prepared by direct amination of the corresponding 4,6-difluoro analog.

3- and 5-Alkoxy and aryloxy analogs can be prepared by reduction of the corresponding 4-azido derivatives, which in turn can be prepared by nucleophilic displacement of the corresponding 4-bromopyridines with $NaN_3$. The required 3- and 5-alkoxy-4-bromopyridines can be prepared according to literature procedures.

6-Alkoxy, alkylthio, aryloxy and heteroaryloxy analogs can be prepared by nucleophilic displacement with alkoxide, thioalkoxide, aryloxide or heteroaryloxide on the appropriate 6-halopyridine.

3- and 5-Alkylthio analogs can be prepared by lithiation of the appropriate chloropyridines at low temperature and sequential treatment with alkyl disulfides and carbon dioxide. Reaction of the resulting picolinic acids with ammonium hydroxide gave the desired products.

6-Cyano analogs can be prepared by amination of the appropriate 4-halo-6-cyanopicolinate. 4-Halo-6-cyanopicolinates can be prepared by action of trimethylsilyl cyanide (TMSCN) on the appropriate pyridine N-oxide, which can be prepared by hydrogen peroxide mediated oxidation of the corresponding pyridine.

3- and 5-Cyano analogs can be prepared by action of KCN on the appropriate fluoropyridine at high temperature. 3- and 5-Fluoro, bromo, iodo and nitro analogs can be prepared by electrophilic reaction of the unsubstituted precursor with positive halogen or nitro sources such as fluorine gas, bromine, iodine and fuming nitric acid respectively.

6-Trifluoromethyl analogs can be prepared by amination of readily available methyl trifluoromethylpicolinate (oxidative halogenation of the 4-position followed by displacement with ammonia or an amine equivalent) followed by chlorination of the 3- and 5-positions.

3- and 5-Trifluoromethyl analogs can be prepared by standard manipulations known to those skilled in the art starting from the known compounds 2-fluoro-3-chloro-5-trifluorometylpyridine and 2,5-dichloro-3-trifluoromethylpyridine.

Substituted ed 4-amino analogs can be prepared by reacting the corresponding 4-halopyridine-2-carboxylate or any other displaceable 4-substituent with the substituted amine.

The compounds of Formula I, obtained by any of these processes, can be recovered by conventional means. Typically, the reaction mixture is acidified with an aqueous acid, such as hydrochloric acid, and extracted with an organic solvent, such as ethyl acetate or dichloromethane. The organic solvent and other volatiles can be removed by distillation or evaporation to obtain the desired compound of Formula I, which can be purified by standard procedures, such as by recrystallization or chromatography.

The compounds of Formula I have bee n found to be useful pre-emergence and post-emergence herbicides. They can be employed at non-selective (higher) rates of application to control a broad spectrum of the vegetation in an area or at lower rates of application for the selective control of undesirable vegetation. Areas of application include pasture and rangelands, roadsides and rights of ways, and crops such as corn, rice and cereals. It i s usually preferred to employ the compounds post-emergence. It is further usually preferred to use the compounds to control a wide spectrum of broadleaf weeds, including Dock species (Rumex spp), Canada thistle (*Cirsium arvense*), pigweed species (Amaranthus spp.), Senna species (Cassia spp.), spurge species (Euphorbia spp), ragweed species (Ambrosia spp.), Sida species (Sida spp.), field bindweed (*Convolvulus arvensis*), and knapweed species(Centaurea spp.), among others. Use of the compounds to control undesirable vegetation in grassy areas is especially indicated. While each of the 4-aminopicolinate compounds encompassed by Formula I is within the scope of the invention, the degree of herbicidal activity, the crop selectivity, and the spectrum of weed control obtained varies depending upon the substituents present. An appropriate compound for any specific herbicidal utility can be identified by using the information presented herein and routine testing.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings and established vegetation.

Herbicidal activity is exhibited by the compounds of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the compounds of Formula I postemergence to relatively immature undesirable vegetation to achieve the maximum control of weeds.

Application rates of about 1 to about 500 g/Ha are generally employed in postemergence operations; for preemergence applications, rates of about 10 to about 1000 g/Ha are generally employed. The higher rates designated generally give non-selective control of a broad variety of undesirable vegetation. The lower rates typically give selective control and can be employed in the locus of crops.

The herbicidal compounds of the present invention are often best applied in conjunction with one or more other herbicides to obtain control of a wider variety of undesirable vegetation. When used in conjunction with other herbicides, the presently claimed compounds can be formulated with the other herbicide or herbicides, tank mixed with the other herbicide or herbicides, or applied sequentially with the other herbicide or herbicides. Some of the herbicides that can be employed in conjunction with the compounds of the present invention include sulfonamides such as metosulam, flumetsulam, cloransulam-methyl, diclosulam and florasulam, sulfonylureas such as chlorimuron, nicosulfuron and metsulfuron, imidazolinones such as imazaquin, imazapic, imazethapyr and imazamox, phenoxyalkanoic acids such as 2,4-D and MCPA, pyridinyloxyacetic acids such as triclopyr and fluroxypyr, carboxylic acids such as clopyralid and dicamba, dinitroanilines such as trifluralin and pendimethalin, chloroacetanilides such as alachlor, acetochlor and metolachlor and other common herbicides including acifluorfen, bentazon, clomazone, fumiclorac, fluometuron, fomesafen, lactofen, linuron, isoproturon, and metribuzin. Particularly preferred combinations are those with florasulam, 2,4-D and fluroxypyr, which, against some weed species, may actually exhibit synergy. A synergistic response may also be obtained with compounds of the present invention when mixed with auxin transport inhibitors such as diflufenzopyr and chlorflurenol. The herbicidal compounds of the present invention can, further, be used in conjunction with glyphosate and glufosinate on glyphosate-tolerant or glufosinate-tolerant crops. It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

The compounds of the present invention can generally be employed in combination with known herbicide safeners, such as cloquintocet, furilazole, dichlormid, benoxacor, mefenpyr-ethyl, fenclorazole-ethyl, flurazole, and fluxofenim, to enhance their selectivity. They can additionally be employed to control undesirable vegetation in many crops that have been made tolerant to or resistant to them or to other herbicides by genetic manipulation or by mutation and selection. For example, corn, wheat, rice, soybean, sugarbeet, cotton, canola, and other crops that have been made tolerant or resistant to compounds that are acetolactate synthase inhibitors in sensitive plants can be treated. Many glyphosate and glufosinate tolerant crops can be treated as well, alone or in combination with these herbicides. Some crops (e.g. cotton) have been made tolerant to auxinic herbicides such as 2,4-dichlorophenoxy-acetic acid. These herbicides may be used to treat such resistant crops or other auxin tolerant crops.

While it is possible to utilize the 4-amino-picolinate compounds of Formula I directly as herbicides, it is preferable to use them in mixtures containing a herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethyl-ammonium chloride; polyethylene glycol esters of fatty acids, such as polyethylene glycol stearate; block copolymers of ethylene oxide and propylene oxide; and salts of mono and dialkyl phosphate esters.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation water, and by other conventional means known to those skilled in the art.

The following Examples are presented to illustrate the various aspects of this invention and should not be construed as limitations to the claims.

EXAMPLES

1. Preparation of 4-Amino-3,6-dichloropyridine-2-carboxylic Acid (Compound 1)

In a 3-liter (L) beaker was added 2000 grams (g) of hot water, 115.1 g of 50 percent by weight NaOH, and 200 g of wet 4-amino-3,5,6-trichloropyridine-2-carboxylic acid (79.4 percent). The solution was stirred for 30 minutes (min), filtered through a paper filter, and transferred to a 5-L feed/recirculation tank. This solution weighed 2315 g and contained 6.8 percent 4-amino-3,5,6-trichloropyridine-2-carboxylic acid. This feed was recirculated at a rate of about 9.46 L/min and a temperature of 30° C. through an undivided electrochemical cell having a Hastelloy C anode and an expanded silver mesh screen cathode. After normal anodization at +0.7 volt (v), the polarity of the cell was reversed and the electrolysis was started. The cathode working potential was controlled at −1.1 to −1.4 v relative to an Ag/AgCl (3.0 M $Cl^-$) reference electrode. While recirculating the feed, a solution of 50 percent NaOH is slowly pumped into the recirculation tank to maintain the NaOH concentration at a 1.5 to 2.0 percent excess. After about 15 hours (hr), the electrolysis was terminated and the cell effluent was filtered through a paper filter. The solution was neutralized with concentrated HCl and concentrated to about 750 g of crude concentrate. The concentrate was warmed to 85° C. with stirring and the pH was adjusted to less than 1 with concentrated HCl over 30 min. The resulting slurry was cooled to ambient temperature and filtered. The filter cake was washed with 3×200 milliliter (mL) portions of water and dried under vacuum at 80° C. The dried product, 118.1 g assayed at 90.6 percent desired product; gas chromatography (GC) indicated about 4 percent 4-amino-3,5,6-trichloropyridine-2-carboxylic acid remaining as an impurity. A purified sample of 4-amino-3,6-dichloropyridine-2-carboxylic acid had a melting point (mp) of 185–187° C. (dec.); $^1$H NMR (DMSO-$d_6$): δ 13.9 (br, 1H), 7.0 (br m, 2H), 6.8 (s,1H); $^{13}$C NMR {$^1$H} (DMSO-$d_6$): δ 165.4 (1C), 153.4 (1C), 149.5 (1C), 147.7 (1C), 111.0 (1C), 108.1 (1C).

2. Preparation of 2-Ethylhexyl 4-amino-3,6-dichloropyridine-2-carboxylate (Compound 2)

To a solution of 2-ethylhexanol (10 mL) and sulfuric acid (1 mL) was added 4-amino-3,6-dichloro-pyridine-2-carboxylic acid (0.0097 mol, 2.0 g). After heating the reaction to reflux overnight, the reaction mixture was cooled, poured into water (75 mL), and extracted with ethyl acetate (75 mL). The organic phase was washed with sodium bicarbonate (75 mL), dried ($Na_2SO_4$), and concentrated. The resulting solid was recrystallized out of dichloromethane and hexane and filtered to give 2-ethylhexyl 4-amino-3,6-dichloropyridine-2-carboxylate (0.0074 mol, 2.36 g) as a crystalline solid (mp 55° C.). $^1$H NMR ($CDCl_3$): δ 0.9 (7 H, m), 1.3 (7 H, m), 1.7 (1 H, m), 4.3 (2 H, d), 5.1 (2 H, bs), 6.7 (1 H, s).

The following esters of 4-amino-3,5,6-trichloro-pyridine-2-carboxylic acid were prepared according to the procedure of Example 2:

methyl 4-amino-3,6-dichloropyridine-2-carboxylate (Compound 3); mp 134–135° C.

ethyl 4-amino-3,6-dichloropyridine-2-carboxylate (Compound 4); mp 98–99° C.

n-propyl 4-amino-3,6-dichloropyridine-2-carboxylate (Compound 5); mp 94–95° C.

i-propyl 4-amino-3,6-dichloropyridine-2-carboxylate (Compound 6); mp 114–115° C.

n-butyl 4-amino-3,6-dichloropyridine-2-carboxylate (Compound 7); mp 78–79° C.

n-pentyl 4-amino-3,6-dichloropyridine-2-carboxylate (Compound 8); mp 71–73° C.

n-hexyl 4-amino-3,6-dichloropyridine-2-carboxylate (Compound 9); mp 65–66° C.

butoxyethyl 4-amino-3,6-dichloropyridine-2-carboxylate (Compound 10); mp 64–7° C. as the monohydrate.

3. Preparation of 4-Amino-3,6-dichloropyridine-2-carboxamide (Compound 11)

To a 250 mL three neck roundbottom flask fitted with a mechanical stirrer were added methyl 750 (10.0 g, 45 mmol) and 28% aq. $NH_4OH$ (35 mL) at 0° C. The suspension was stirred vigorously for 24 hr while warming gradually to 25° C. The suspension was suction filtered, and the filter cake was washed on the filter with cold water (2×100 mL). After air drying on the filter, the analytically pure white solid product was collected to give 4-amino-3,6-dichloropyridine-2-carboxamide 11 (8.58 g, 92% yield); mp 240–241° C.

4. Preparation of Methyl N-acetyl 4-amino-3,6-dichloropyridine-2-carboxylate (Compound 12) and N,N-diacetyl 4-amino-3,6-dichloropyridine-2-carboxylate (Compound 13)

A solution of acetic anhydride (75 mL) and methyl 4-amino-3,6-dichlororpyridine-2-carboxylate (0.00904 mol, 2.0 g) was stirred and heated to reflux overnight. The solution was cooled, concentrated, taken up in ethyl acetate (100 mL), and washed with water (100 mL). The organic phase was washed with saturated sodium bicarbonate (100 mL), dried ($Na_2SO_4$), and concentrated. The solution was purified by chromatography on silica gel. The front running spot was isolated and gave a yellow oil identified as the diacylated 4-amide Compound 13 (0.0023 mol, 0.700 g). $^1$H NMR 2.2 (6 H, s), 3.9 (3 H, s), 7.3 (1 H, s). The second spot gave a yellow solid identified as the monoacylated 4-amide compound 12(0.0035 mol, 0.920 g); mp 102–103° C.

5. Preparation of 4-Amino-6-bromo-3-chloropyridine-2-carboxylic Acid (Compound 14)

A. Methyl 6-Bromo-3-chloropyridine-2-carboxylate, N-oxide

To a solution of methyl 6-bromo-3-chloropyridine-2-carboxylate (0.13 mol, 32.1 g) in trifluoroacetic acid (75 mL) and trifluoroacetic anhydride (40 mL) was cautiously added 50% hydrogen peroxide (0.17 mol, 13 g). The reaction exothermed to reflux. After stirring for 30 min, the solution was poured into a mixture of ice and 10 percent sodium bisulfite (150 mL). The resulting solid was collected and dried in vacuo to give a white solid (0.08 mol, 21.4 g). $^{1}H$ NMR ($CDCl_3$): δ 4.1 (3H, s), 7.3 (1H, d), 7.7 (1H, d).

B. Methyl 6-Bromo-3-chloro-4-nitropyridine-2-carboxylate, N-oxide

To a solution of fuming nitric acid (10 mL) and fuming sulfuric acid (10 mL) was added methyl 6-bromo-3-chloropyridine-2-carboxylate, N-oxide and the reaction was heated to 70° C. in an oil bath for 4 hr. The mixture was poured over ice water (100 mL) and extracted with ethyl acetate (3x75 mL) and the combined extracts were back-washed with brine, dried ($Na_2SO_4$) and concentrated. The dark oil was chromatographed over silica in 4:1 EtOAc/hexane to give methyl 6-bromo-3-chloro-4-nitropyridine-2-carboxylate, N-oxide (0.007 mol, 2.2 g). $^{1}H$ NMR ($CDCl_3$): δ 4.1 (3H, s), 8.4 (1H, s).

C. Methyl 4-amino-6-bromo-3-chloropyridine-2-carboxylate

To a solution of titanium tetrachloride (0.015 mol, 2.8 g) in tetrahydrofuran (50 mL) was added lithium aluminum hydride (0.0175 mol, 0.7 g). The black slurry was stirred 15 min before adding methyl 6-bromo-3-chloro-4-nitropyridine-2-carboxylate, N-oxide (0.007 mol, 2.3 g) in THF (25 mL). The solution was stirred 1 hr before pouring into 1:1 $H_2O/NH_4OH$ and filtering. The filtrate was extracted with EtOAc (2x75 mL). The organic phase was dried ($Na_2SO_4$), and concentrated. The red solid was chromatographed over silica in 4:1 EtOAc/hexane to give methyl 4-amino-6-bromo-3-chloropyridine-2-carboxylate (0.003 mol, 0.8 g); mp 194–5° C. $^{1}H$ NMR($CDCl_3$): δ 3.95 (3H, s), 5.3 (2H, bs), 6.9 (1H, s).

D. 4-Amino-6-bromo-3-chloropyridine-2-carboxylic Acid (Compound 14)

To methyl 4-amino-6-bromo-3-chloropyridine-2-carboxylate (200mg; 0.8 mmol) in 10 mL of methanol was added excess 2N NaOH (10 mL). The mixture was stirred for 1 hr at ambient temperature and then evaporated to dryness in vacuo. The residue was dissolved in water and diethyl ether. After separation of the phases, the aqueous layer was acidified with 1N HCl to a pH=2. The aqueous layer was evaporated to dryness and the residue was dissolved in 50 mL of methanol and filtered. The filtrate was evaporated under reduced pressure and the residue was triturated with 5 percent diethyl ether in petroleum ether to give 70 mg of 4-amino-6-bromo-3-chloropyridine-2-carboxylic acid, mp 182–183° C.

6. Preparation of Methyl 4-Amino-3-chloro-6-fluoropyridine-2-carboxylate (Compound 15)

A. Methyl 3-Chloro-4,6-difluoropyridine-2-carboxylate

To a solution of methyl 3,4,6-trichloropyridine-2-carboxylate (0.010 mol, 2.4 g) in DMSO (10 mL) was added cesium fluoride (0.038 mol, 3.8 g) and the suspension was heated for 2 hr at 100° C. The reaction mixture was dissolved in dilute HCl and extracted with ethyl acetate (EtOAc). The organic layer was treated with (trimethylsilyl) diazomethane ($TMSCHN_2$) to re-esterify any hydrolyzed ester. The mixture was concentrated and the resultant residue was chromatographed over silica with 10 percent EtOAc/hexane to give methyl 3-chloro-4,6-difluoropyridine-2-carboxylate (0.0072 mol, 1.5 g). $^{1}H$ NMR ($CDCl_3$): δ 4.00 (3H, s ), 6.95–6.90 (1H, m). $^{19}F$ NMR {$^{1}H$}: δ −65.0 (d, J=17 Hz), 95.8 (d, J=17 Hz).

B. Methyl 4-Amino-3-chloro-6-fluoropyridine-2-carboxylate (Compound 15)

Sodium azide (0.0086 mol, 0.60 g) was added to a solution of methyl 3-chloro-4,6-difluoropyridine-2-carboxylate (0.0072 mol, 1.5 g) in 15 mL dimethyl formamide (DMF). The solution was stirred 10 min at ambient temperature before pouring into 350 mL water and extracting the aqueous mixture with EtOAc (2x100 mL). The organic phase was dried ($Na_2SO_4$) and then treated with excess $NaBH_4$ for 30 min. The excess $NaBH_4$ was quenched with aqueous EtOH and the mixture was diluted with water (200 mL). The organic layer was separated and the aqueous layer extracted with EtOAc (2x200 mL). The combined organic layers were dried ($Na_2SO_4$) and concentrated to an off-white powder which was purified by reversed-phase HPLC to give methyl 4-amino-3-chloro-6-fluoropyridine-2-carboxylate (0.0059 mol, 1.2 g). $^{1}H$ NMR($CDCl_3$): δ 3.95 (3H, s), 5.2–5.1 (2H, bs), 6.36 (1H, s). $^{19}F$ NMR {$^{1}H$}: δ −72.7.

7. Preparation of 4-Amino-3,5-difluoro-6-bromopyridine-2-carboxylic Acid (Compound 16)

A. Preparation of 4-Amino-3,5,6-trifluoro-2-cyanopyridine

To a solution of 3,4,5,6-tetrafluoro-2-cyanopyridine in DMF (75 mL) at 0C was slowly added concentrated ammonium hydroxide (15 mL). The reaction was stirred and additional 15 min and the solution was diluted with water (150 mL). The solid was collected and air dried to give 4-amino-3,5,6-trifluoro-2-cyanopyridine (25.5 g, 0.16 mol, 92%); mp 291–30 C.

B. Preparation of Methyl, 4-Amino-6-bromo-3,5-difluoropyridine-2-carboxylate (Compound 16)

A solution of 4-amino-3,5,6-trifluoro-2-cyanopyridine (19 g, 0.12 mol) in thirty percent hydrogen bromide in acetic acid (150 mL) was place in a Paar bomb and heated to 110° C. for 3 hr. The reaction was diluted with water (300 ml) and the solid (4-amino-6-chloro-3,5-difluoropyridine-2-carboxyamide) was collected. This material, without further purification, was slurried in methanol (500 ml) and concentrated hydrochloric acid added. The slurry was heated under reflux for 4 hr and, after cooling to room temperature, diluted with water (1,000 mL) and the solid collected and dried to give methyl 4-amino-6-bromo-3,5-difluoropyridine-2-carboxlate (9.6 g, 0.04 mol, 25%); mp 110–111° C.

8. Preparation of 4-Amino-3,6-dibromopyridine-2-carboxylic Acid (Compound 17)

3,4,5,6-Tetrabromopyridine-2-carboxamide (5.0 g) was selectively aminated with ammonia gas at RT in 100 mL methanol. The resultant solution was concentrated to an off-white solid and hydrolyzed with conc. sulfuric acid (25 mL) at 140° C. for 3 hr. the mixture was made basic with NaOH, extracted with EtOAc (2x100 mL), acidified and filtered to give 1.4 g of pure 4-amino-3,6-dibromopyridine-2-carboxylic acid; mp 205° C. dec.

9. Preparation of Methyl 4-Amino-3,5,6-tribromopyridine-2-carboxylate (Compound 18)

Methyl 4-amino-3,5,6-tribromopyridine-2-carboxylate was prepared by amination of methyl 3,4,5,6-tetrabromopyridine-2-carboxylate following the procedure of Example 6B. $^{1}H$ NMR($CDCl_3$): δ 3.95 (3H, s), 6.9–6.8 (2H, bs).

10. Preparation of 4-Amino-3,6-dichloro-5-fluoropyridine-2-carboxylic Acid (Compound 19)

To a solution of 4-amino-3,6-dichloropyridine-2-carboxylate (1.5 g, 6.8 mmol) in 20 mL of dry acetonitrile was added 1-(chloromethyl)-4-fluoro-1,4-diazoniabicyclo [2.2.2]octane bis (tetrafluoroborate) (Selectfluor™ from Aldrich Chemical Company, Inc.; 2.9 g, 2.59 mmol [$F^+$]/g). The resulting mixture was heated at reflux for 3 hr, then allowed to cool to room temperature. This material was taken up in $Et_2O$ and washed with $H_2O$. The organic layer was dried over $MgSO_4$, filtered and concentrated to yield a brown oil. The crude product was purified via reverse phase HPLC (50% acetonitrile/water) to give 0.37 g of white solid which was stirred in 1N NaOH for 1 hr then made acidic with conc. HCl. The precipitated white solid was collected with suction, washed with $H_2O$ and dried under vacuum to give 170 mg of 4-amino-3,6-dichloro-5-fluoropyridine-2-carboxylic acid (11% yield); mp 214° C. dec.

11. Preparation of 4-Amino-3,6-dichloro-5-bromopyridine-2-carboxylic Acid (Compound 20)

To a solution of methyl 4-amino-3,6-dichloropyridine-2-carboxylate (18 g, 81 mmol) in 100 mL fuming sulfuric acid was added bromine (15 mL, excess). The resulting mixture was heated to 70° C. for 30 min, then allowed to cool to room temperature. This material was poured into ice water (1000 mL) and extracted with EtOAc (4×500 mL). The combined organic extracts were dried ($MgSO_4$), filtered and concentrated to yield a brown solid. The crude product was purified via reverse phase HPLC (50% acetonitrile/water) to give 21 g of 4-amino-3,6-dichloro-5-bromopyridine-2-carboxylic acid as a white solid (91% yield); mp 201–202° C.

12. Preparation of 4-Amino-3,6-dichloro-5-trifluoromethylpyridine-2-carboxylic Acid (Compound 21)

A solution of 4-amino-3,6-dichloro-5-trifluoromethyl-2-cyanopyridine (0.5 g, 1.96 mmol) in 10 mL of 85% $H_2SO_4$ was stirred at 140° C. for 0.5 hr. The reaction mixture was allowed to cool and added to ice. The precipitated white solid was collected with suction, rinsed several more times with water and allowed to air dry to give 0.33 g of product as a white solid (61.4% yield); mp 173° C.

13. Preparation of 4-Amino-3,6-dichloro-5-methoxypyridine-2-carboxylic Acid (Compound 22)

A. Methyl 3-Chloro-5-methoxypyridine-2-carboxylate, N-oxide

In a dry 3-neck round bottom flask was added methyl 3,5-dichloropyridine-2-carboxylate, N-oxide (5.0 g, 22.5 mmol) to 25 mL of methanol to give a slurry. A 25% solution of sodium methoxide in methanol (5.40 mL, 23.62 mmol) was added and heated to reflux for 1.5 h. The reaction mixture was diluted in ethyl acetate and added to $H_2O$. The layers were separated and the aqueous layer was saturated with brine and extracted 2 more times in ethyl acetate. The combined organic layers were dried ($MgSO_4$) and concentrated to give a white solid. Purification by column chromatography (silica gel) using an eluent of 50% $Et_2O$/Petroleum ether (1.5 L) then 100% $Et_2O$ to give 1.76 g of a white solid; mp 154–156° C.

B. Methyl 3-Chloro-5-methoxy-4-nitropyridine-2-carboxylate, N-oxide

To methyl 3-chloro-5-methoxypyridine-2-carboxylate, N-oxide (1.41 g, 5.97 mmol) in $H_2SO_4$ cooled to 0C was slowly added a 50/50 mixture of 30% oleum and fuming $HNO_3$. Reaction mixture stirred for 30 min at room temperature and then heated to 70° C. for 3 days. The reaction mixture was diluted with ethyl acetate and cooled to 0° C. Saturated sodium bicarbonate was carefully added and the layers were separated. Aqueous layer was washed 2 more times with ethyl acetate. The combined organic layers were dried ($MgSO_4$) and concentrated to dryness. Purification by column chromatography (silica gel) using an eluent of 20% ethyl acetate/hexane gave 300 mg of a yellow solid; mp 160° C.

C. Methyl 3,6-Dichloro-5-methoxy-4-nitropyridine-2-carboxylate

To methyl 3-chloro-5-methoxy-4-nitro-pyridine-2-carboxylate, N-oxide (0.300 g, 1.12 mmol) in 5 mL of chloroform was added $PCl_3$ (0.664 mL, 7.62 mmol). The reaction mixture was heated to reflux for 8 hr and then concentrated to dryness in vacuo to give 300 mg of a white solid.

D. Methyl 4-Amino-3,6-dichloro-5-methoxypyridine-2-carboxylate

To methyl 3,6-dichloro-5-methoxy-4-nitropyridine-2-carboxylate (0.300 g, 1.06 mmol) in 5 mL of ethyl acetate was added $SnCl_2 \times 2H_2O$ (1.60 g, 7.1 mmol). The reaction mixture was heated to 70° C. for 30 min and then cooled to room temperature. Saturated sodium bicarbonate and a saturated solution of $KHF_2$ were added to reaction mixture. The mixture was extracted with ethyl acetate and the layers were separated. The aqueous layer was washed 2 more times with ethyl acetate. The combined organic layers were dried ($MgSO_4$) and concentrated to dryness to give 0.250 g of a yellow solid.

E. 4-Amino-3,6-dichloro-5-methoxypyridine-2-carboxylic Acid (Compound 22)

4-Amino-3,6-dichloro-5-methoxypyridine-2-carboxylic acid was prepared by saponification of the methyl ester according to the procedure of Example 17(D); mp 154–156° C.

14. Preparation of 4-Amino-3,6-dichloro-5-methylthiopyridine-2-carboxylic Acid (Compound 23)

4-Amino-3,6-dichloro-5-methylthiopyridine-2-carboxylic acid was prepared by analogy to the preparation of 4-amino-3,6-dichloro-5-methoxypyridine-2-carboxylic acid following the procedure of Example 13 using sodium thiomethoxide instead of sodium methoxide; mp 160° C. dec.

15. Preparation of 4-Amino-3,6-dichloro-5-phenylthiopyridine-2-carboxylate (Compound 24)

4-Amino-3,6-dichloro-5-phenylthiopyridine-2-carboxylic acid was prepared by analogy to the preparation of 4-amino-3,6-dichloro-5-methoxypyridine-2-carboxylic acid following the procedure of Example 13 using sodium thiophenoxide instead of sodium methoxide; mp 160° C. dec.

16. Preparation of Methyl 4-Amino-3,6-dichloro-5-nitropyridine-2-carboxylate (Compound 25)

To a solution containing 4-amino-3,6-dichloropyridine-2-carboxylic acid (0.5 g, 2.43 mmol) and 10 mL of conc. $H_2SO_4$ was added dropwise a mixture of conc. $HNO_3$/$H_2SO_4$ (1 mL/1 mL) at RT. After stirring for 5 min, the reaction mixture was added to ice and the solid was collected by vacuum filtration. The resulting solid was dissolved in 20% MeOH/EtOAc and trimethylsilyl diazomethane ($TMSCHN_2$) was then added until reaction was complete. Reaction mixture was concentrated under reduced pressure, taken up in $Et_2O$ and washed with aqueous $NaHCO_3$, dried over $MgSO_4$, filtered and concentrated to give a brown oil. The crude product was purified by chromatography, eluting with 10% ethyl acetate-hexane to give 80 mg of the methyl ester as a yellow solid; mp 127–8° C.

17. Preparation of 4-N-Methylamino-3,6-dichloropyridine-2-carboxylic Acid (Compound 26)

A. Methyl 3,6-Dichloropyridine-2-carboxylate

To a 3-neck round bottom flask equipped with a reflux condenser was added 3,6-dichloropyridine-2-carboxylic acid (50.0 g, 260.42 mmol) in methanol (200 mL). $HCl_{(g)}$ was bubbled in until solution became saturated and stirred at room temperature for 2 hr. The solution was concentrated to dryness in vacuo. Diethyl ether was added to make a slurry that was subsequently added to a flask filled with a 1:1 mixture of saturated sodium bicarbonate/diethyl ether and stirred for 10 min. The aqueous phase was extracted with diethyl ether (3×300 mL). The combined extracts were dried ($MgSO_4$) and concentrated to give 46.6 g of a light yellow solid. $^1H$ NMR($CDCl_3$): δ 4.00 (s, 3H); 7.41 (d, 1H); 7.80 (d, 1H).

B. Methyl 3,6-Dichloropyridine-2-carboxylate, N-oxide

Methyl 3,6-dichloropicolinate (20.0 g, 97.07 mmol) was dissolved in a minimum amount of trifluoroacetic acid (TFA). In a separate flask was stirred trifluoroacetic anhydride (TFAA, 38 mL) and 50% $H_2O_2$ (9.9 g, 145.61 mmol) which was added to the TFA solution. The reaction mixture was stirred at reflux for 1 hr and concentrated to dryness. The orange oil was dissolved in ethyl acetate and saturated sodium bicarbonate. The phases were separated and the aqueous phase was extracted with ethyl acetate (2×200 mL). The combined extracts were dried ($MgSO_4$) and concentrated to a yellow solid. Purification by column chromatography (silica gel) using an eluent of 50% ethyl acetate/hexane gave 12.13 g of a yellow solid. $^1H$ NMR ($CDCl_3$): δ 4.00 (s, 3H); 7.25 (d, 1H); 7.50 (d, 1H).

C. Methyl 3,4,6-Trichloropyridine-2-carboxylate

To methyl 3,6-dichloropicolinate N-oxide (5.0 g, 22.52 mmol) dissolved in 15 mL of acetonitrile was added $POC_{13}$ (4.20 mL, 45.04 mmol). The reaction mixture was stirred at reflux for 5 hr, cooled to room temperature and concentrated to dryness in vacuo. The resultant orange oil was dissolved in diethyl ether. Carefully, saturated sodium bicarbonate was added and the aqueous phase was extracted with diethyl ether (2×100 mL). The combined extracts were dried ($MgSO_4$) and concentrated to dryness. Purification by column chromatography (silica gel) using an eluent of 20% ethyl acetate/hexane gave 5.89 g of a light yellow solid. $^1H$ NMR($CDCl_3$): δ 4.00 (s, 3H); 7. 55 (s, 1H).

D. 3,4,6-Trichloropyridine-2-carboxylic Acid

To methyl 3,4,6-Trichloropicolinate (3.57 g, 14.85 mmol) in 20 mL of methanol was added 1N NaOH (14.85 mL, 14.85 mmol). The reaction mixture was stirred at room temperature for 1 hr and then concentrated to dryness in vacuo. 100 mL each of diethyl ether and $H_2O$ were added. Aqueous layer was acidified with 1N HCl until pH=2. Methylene chloride was added and the aqueous phase was extracted with additional $CH_2Cl_2$ (2×100 mL). The combined extracts were dried ($MgSO_4$) and concentrated to give 3.13 g of a white solid. $^1H$ NMR($CDCl_3$): δ 7.50 (s, 1H).

E. 4-N-Methylamino-3,6-dichloropyridine-2-carboxylic Acid (Compound 26)

3,4,6-Trichloropyridine-2-carboxylic acid (1.56 g, 6.89 mmol) was dissolved in methylamine and placed in a Parr bomb at 80° C. for 2 days. The reaction mixture was cooled to room temperature and diluted with ethyl acetate. 1N HCl was added until pH=2. The aqueous phase was extracted with ethyl acetate (2×50 mL) and the combined extracts were dried ($MgSO_4$) and concentrated to dryness. Desired product was triturated from 5% diethyl ether/pet ether; the solid was filtered and dried to give 0.600 g of a light yellow solid. $^1H$ NMR($CDCl_3$): δ 2.75 (s, 3H); 5.70 (s, 1H); 6.30 (s, 1H); mp 170–172° C.

The following N-alkyl analogs of 4-amino-3,6-dichloropyridine-2-carboxylic acid were prepared according to the procedure of Example 17:

4-N-ethylamino-3,6-dichloropyridine-2-carboxylic acid (Compound 27); mp 136–137° C.

4-N-isopropylamino-3,6-dichloropyridine-2-carboxylic acid (Compound 28); mp 146–147° C.

4-N-butylamino-3,6-dichloropyridine-2-carboxylic acid (Compound 29); mp 96–97° C.

4-N-allylamino-3,6-dichloropyridine-2-carboxylic Acid (Compound 30); mp 128–131° C.

4-N-hydroxyethylamino-3,6-dichloropyridine-2-carboxylic acid (Compound 31); mp 140–141° C.

4-N-methoxyethylamino-3,6-dichloropyridine-2-carboxylic acid (Compound 32); mp 97–99° C. 4-N,N-dimethylamino-3,6-dichloropyridine-2-carboxylic acid (Compound 33); mp 110° C.

4-N-hydroxy-N-methyl-amino-3,6-dichloropyridine-2-carboxylic acid (Compound 34); mp 140–1° C.

4-N-methoxy-N-methyl-3,6-dichloropyridine-2-carboxylic acid (Compound 35); mp 98–99° C.

4-pyrrolidino-3,6-dichloropyridine-2-carboxylic acid (Compound 36); mp 153–5° C. 4-pyrrolo-3,6-Dichloropyridine-2-carboxylic acid (Compound 37); mp 155–156° C.

18. Preparation of Methyl 4-Azido-6-bromo-3-chloropyridine-2-carboxylic Acid (Compound 38)

To a solution of methyl 4,6-dibromo-3-chloropyridine-2-carboxylate (6.0 g 0.018 mol) in DMF (50 mL) was added sodium azide (2.0 g 0.03 mol) and the solution warmed to 50° C. for 1 hr. The reaction was diluted with water (200 mL) and cooled to 0° C. for 1 hr. The solid was collected to give methyl 4-azido-6-bromo-3-chloropyridine-2-carboxylate (4.4 g, 0.012 mol, 66%); mp 84–86° C.

19. Preparation of 4-Nitro-3,6-dichloropyridine-2-carboxylic Acid (Compound 39)

Methyl 3,6-dichloropyridine-2-carboxylate N-oxide (5.0 g, 22.52 mmol) was dissolved in a minimum amount of $H_2SO_4$. The mixture was cooled in an ice/water bath and to it was slowly added 30% oleum (9.6 mL) and fuming $HNO_3$ (9.6 mL), gradually heated to 65° C. and stirred for 48 hr. The cooled reaction mixture was diluted with ethyl acetate (200 mL) and to it was carefully added saturated sodium bicarbonate. The product was extracted with ethyl acetate (2×150 mL) and the combined extracts were dried ($MgSO_4$) and concentrated to give 0.10 g of a yellow solid; mp 192–193° C.

20. Preparation of 4-N,N-Dimethylformamidino-3,6-dichloropyridine-2-carboxylic Acid (Compound 40)

To a suspension of methyl 4-amino-3,6-dichloropyridine-2-carboxylic acid (2.07 g, 10.0 mmol)in THF (50 mL) was added 5.0 eq N,N-dimethylformamide dimethyl acetal (50 mmol). The mixture was heated to 50° C. for 1 hr during which time the suspension became a homogeneous solution. The cooled reaction mixture was concentrated in vacuo, triturated with hexanes to a white amorphous solid and dried under high vacuum to give 2.5 g of a highly hygroscopic white powder (95% yield); $^{1}$H NMR (DMSO) δ 8,21 (1H, s), 7.95 (1H, s), 3.25 (3H, s), 3.17 (3H, s).

21. Preparation of 4-Amino-6-bromo-3-methoxypyridine-2-carboxylic Acid (Compound 41)

A. Methyl 4,6-Dibromo-3-methoxypyridine-2-carboxylate

To methyl 4,6-dibromo-3-hydroxypyridine-2-carboxylate 3.98 g (3.98 g, 12.81 mmol) in 40 mL of acetone was added $K_2CO_3$ (2.0 g, 14.47 mmol) and dimethyl sulfate (1.20 mL, 12.37 mmol). The reaction mixture was refluxed overnight and concentrated to dryness. The residue was dissolved in ethyl acetate and saturated sodium bicarbonate. The phases were separated and the aqueous phase was extracted with ethyl acetate (3×100 mL). The combined extracts were dried ($MgSO_4$) and concentrated to dryness. The residue was purified by chromatography (silica gel). Elution with 15% ethyl acetate/hexane gave 0.980 g, of a white solid. $^{1}$H NMR($CDCl_3$): δ 3.95 (s, 3H); 3.90 (s, 3H); 7.80 (s, 1H).

B. Methyl 4-Azido-6-bromo-3-methoxypyridine-2-carboxylate

Methyl 4,6-dibromo-3-methoxypyridine-2-carboxylate (0.980 g, 3.02 mmol) was dissolved in a minimum amount of DMF. Slowly sodium azide (0.216 g, 3.32 mmol) was added followed by $H_2O$ to form a homogeneous solution. The reaction mixture was heated to 60° C. and stirred for 2 days. Reaction mixture added to a flask filled with ice water and extracted with ethyl acetate (3×50 mL). Extracts were combined and back washed with $H_2O$, dried ($MgSO_4$) and concentrated to give 0.500 g of an orange oil. $^{1}$H NMR ($CDCl_3$): δ 3.90 (s, 3H); 3.95 (s, 3H); 7.20 (s, 1H).

C. Methyl 4-Amino-6-bromo-3-methoxypyridine-2-carboxylate

To methyl 4-azido-6-bromo-3-methoxypyridine-2-carboxylate (0.500 g, 1.74 mmol) in 10 mL of methanol was added $NaBH_4$ (0.046 g, 1.22 mmol). The reaction mixture was stirred at room temperature for 10 min. Ethyl acetate and water were added and the phases were separated. The organic phase was washed with $H_2O$, dried ($MgSO_4$) and concentrated to dryness in vacuo. The residue was purified by chromatography (silica gel). Elution with 100% ethyl acetate gave 0.300 g of a white solid. $^{1}$H NMR($CDCl_3$): δ 3.90 (s, 1H); 3.95 (s, 1H); 4.60 (s, 2H); 6.85 (s, 1H).

D. 4-Amino-6-bromo-3-methoxypyridine-2-carboxylic Acid (Compound 41)

To methyl 4-amino-6-bromo-3-methoxypyridine-2-carboxylate (0.300 g, 1.15 mmol) in 10 mL of methanol was added 1N NaOH (1.15 mL, 1.15 mmol). The reaction mixture was stirred at room temperature for 1 hr and concentrated to dryness in vacuo. Diethyl ether and $H_2O$ were added. The aqueous layer was acidified with 1N HCl until pH=2 and concentrated to dryness. Methanol (50 mL) was added to the white solid. The mixture was filtered and the filtrate concentrated to dryness. Triturating with 5% diethyl ether/pet ether gave 0.180 g of a light pink solid. $^{1}$H NMR(DMSO): δ 3.60 (s, 3H); 6.80 (S, 1H).

22. Preparation of 4-Amino-6-bromo-5-chloro-3-methoxypyridine-2-carboxylic Acid (Compound 42)

A. Methyl 4-Amino-6-bromo-5-chloro-3-methoxypyridine-2-carboxylate

To methyl 4-amino-6-bromo-3-methoxypyridine-2-carboxylate (1.45 g, 5.56 mmol) in 10 mL of acetonitrile was added sulfuryl chloride, in excess, via pipette until the solution remained yellow. The solution was heated to reflux for 5 min. The reaction mixture was added to saturated sodium bicarbonate and aqueous phase was extracted with diethyl ether (3×). The combined organic extracts were dried ($MgSO_4$), filtered and concentrated in vacuo to give a yellow solid. Solid was washed in 10% diethyl ether/petroleum ether and solid filtered to give 0.580 g of a white solid.

B. 4-Amino-6-bromo-5-chloro-3-methoxypyridine-2-carboxylic Acid (Compound 42)

To methyl-4-amino-6-bromo-5-chloro-3-methoxypyridine-2-carboxylate (0.300 g, 1.02 mmol) in 10 mL of methanol was added 1 N NaOH (1.10 mL, 1.10 mmol). The reaction mixture was stirred at room temperature for 4 hr and was then concentrated to dryness in vacuo. The resulting aqueous layer was acidified with concentrated HCl. The white solid was collected by filtration and was rinsed with $H_2O$. The solid was dried at 50° C. under vacuum to give 0.230 g of a white fluffy solid; mp 154–156° C.

23. Preparation of 4-Amino-5,6-dichloro-3-fluoropyridine-2-carboxylic Acid (Compound 43)

A. 4-Amino-5,6-dichloro-2-trichloromethylpyridine

To a solution of 4,5,6-trichloro-2-trichloromethylpyridine (2 g, 6.7 mmol) in aqueous DMF was added $NaN_3$ (0.5 g, 7.7 mmol). The resulting mixture was heated at 70° C. for 2 hr, added to $H_2O$ and extracted (3x) with $Et_2O$. Organic layer was concentrated to yield a white solid, which was dissolved in 10 mL of MeOH. Excess $NaBH_4$ was added and the reaction mixture was stirred at room temperature for 0.5 hr. This material was added to $H_2O$, extracted (3×) with $Et_2O$, dried over $MgSO_4$ and concentrated in vacuo. The resulting solid was washed several times with hexane to give 1.3 g of 4-amino-5,6-dichloro-2-trichloromethylpyridine.

B. 4-Amino-5,6-dichloro-3-fluoropyridine-2-carboxylic Acid (Compound 43)

To a solution of 4-amino-5,6-dichloro-2-trichloromethylpyridine (1.25 g, 4.46 mmol) in 20 mL of dry acetonitrile was added Selectfluor™ (1.9 g, 2.59 mmol $[F^+]$/g). The resulting mixture was heated at reflux for 72 hr, then allowed to cool to room temperature. This material was taken up in $Et_2O$ and washed with $H_2O$. The organic layer was dried over $MgSO_4$, filtered and concentrated to yield a dark oil. The crude product was purified via reverse phase HPLC (75% acetonitrile/water) to give 0.2 g of white solid which was stirred in 80% $H_2SO_4$ at 155° C. for 0.5 hr. Reaction mixture was allowed to cool and extracted several times with 10% $MeOH/CH_2Cl_2$. Organic layer was dried over $MgSO_4$, filtered and concentrated to give a white solid which was washed several times with hexane-diethyl ether to give 60 mg of 4-amino-5,6-dichloro-3-fluoropyridine-2-carboxylic acid; mp 208° C. dec.

24. Preparation of 4-Amino-3-bromo-6-chloropyridine-2-carboxylic Acid (Compound 44)

A. Methyl 3-Bromo-4-chloropyridine-2-carboxylate

To a solution of 3-bromo-4-chloropyridine-2-carboxylic acid (1.75 g, 7.4 mmol) in MeOH was added anhydrous HCl. The resulting mixture was stirred at room temperature for 18 hr. The reaction mixture was concentrated to give a solid, which was partitioned between $Et_2O$ and saturated $NaHCO_3$. Organic layer was dried over $MgSO_4$, filtered and concentrated to give a brown residue. This material was purified via flash column chromatography to yield 1.35 g of product as a pale yellow oil.

B. Methyl 3-Bromo-4,6-dichloropyridine-2-carboxylate

To a solution of methyl 3-bromo-4-chloropyridine-2-carboxylate (1.35 g, 5.4 mmol) in 5 mL of TFA was added 30% $H_2O_2$ (1 g, 9.8 mmol). The resulting mixture was stirred at 75° C. for 0.5 hr and allowed to cool to room temperature. $Et_2O$ was added and the organic layer was washed carefully with saturated $NaHCO_3$, dried over $MgSO_4$, filtered and concentrated to give the corresponding N-Oxide intermediate as a white solid. This material was taken up in acetonitrile (5 mL), $POC_{13}$ (2–3 mL) and heated at reflux for 2 hr. The reaction mixture was allowed to cool, added to $Et_2O$ and washed carefully with saturated $NaHCO_3$, dried over $MgSO_4$, filtered and concentrated to give 0.9 g of product as a light brown oil. This material was sufficiently pure to carry on to the next step.

C. 4-Amino-3-bromo-6-chloropyridine-2-carboxylic Acid (Compound 44)

To a solution of methyl 3-bromo-4,6-dichloropyridine-2-carboxylate (0.9 g, 3.2 mmol) in aqueous DMF was added $NaN_3$ (0.25 g, 3.8 mmol). The resulting mixture was heated at 60° C. for 1 hr, added to $H_2O$ and extracted (3×) with $Et_2O$. Organic layer was concentrated to yield a white solid, which was dissolved in 10 mL of MeOH. Excess $NaBH_4$ was added and the reaction mixture stirred at room temperature for 0.5 hr. This material was added to $H_2O$, extracted (3×) with $Et_2O$, dried over $MgSO_4$ and concentrated. The resulting solid was stirred in 1N NaOH for 1 hr, made acidic with conc. HCl and concentrated to dryness. This material was extracted with MeOH, concentrated to give 220 mg of 4-amino-3-bromo-6-chloropyridine-2-carboxylic acid; mp 175° C. dec.

25. Preparation of 4-Amino-3,5-dichloro-6-trifluoromethylpyridine-2-carboxylic Acid (Compound 45)

A. Methyl 4-Chloro-6-trifluoromethylpyridine-2-carboxylate

To a solution of 6-trifluoromethylpicolinic acid (8.6 g, 45 mmol; prepared from the corresponding 6-trifluoromethyl-2-cyanopyridine) in 25 mL of TFA was added 30% $H_2O_2$ (7.8 g, 67.5 mmol). Reaction mixture was stirred at 70° C. for 18 h and concentrated to give 8.0 g of the N-oxide. This material was stirred in HCl/MeOH solution for 18 hr. The reaction mixture was concentrated to give an oily residue which was partitioned between $Et_2O$ and saturated $NaHCO_3$. The organic layer was dried over $MgSO_4$, filtered and concentrated to give 5.0 g of a yellow oil. Neat $POC_{13}$ was added and stirred at reflux for 2 hr. The mixture was allowed to cool, added carefully to saturated $NaHCO_3$ and extracted (3×) with $Et_2O$. The organic layer was dried over $MgSO_4$, filtered and concentrated to give a brown solid. This material was purified via flash column chromatograph to give 2.64 g of product as a white solid; mp 62–3° C.

B. Methyl 4-Amino-6-trifluoromethylpyridine-2-carboxylate

To a solution of methyl 4-chloro-6-trifluoromethylpyridine-2-carboxylate (2.44 g, 10.2 mmol) in aqueous DMF was added $NaN_3$ (0.7 g, 10.8 mmol). The resulting mixture was heated at 70° C. for 18 hr, added to $H_2O$ and extracted (3×) with $Et_2O$. The organic layer was concentrated to yield a white solid that was dissolved in 10 mL of MeOH. Excess $NaBH_4$ was added and the reaction mixture stirred at RT for 0.5 hr. This material was added to $H_2O$, extracted (3×) with $Et_2O$. The extract was dried over $MgSO_4$ and concentrated. The resulting residue was purified via flash column chromatography to give 0.95 of product as a white solid; mp 114° C.

C. Methyl 4-Amino-3-5-dichloro-6-trifluoromethylpyridine-2-carboxylate

To a solution of methyl 4-amino-6-trifluoromethylpyridine-2-carboxylate (0.75 g, 3.4 mmol) in 5 mL of dry acetonitrile was added $SO_2Cl_2$ (0.55 ml, 6.8 mmol). The resulting mixture was heated at reflux for 0.5 hr, then allowed to cool to room temperature. This material was taken up in $Et_2O$ and washed with saturated $NaHCO_3$. The organic layer was dried over $MgSO_4$, filtered and concentrated to give solid. The crude material was purified via flash column chromatography to yield 0.28 g of product as a white solid; mp 135–6° C.

D. Preparation of 4-Amino-3,5-dichloro-6-trifluoromethylpyridine-2-carboxylate (Compound 45)

To a solution of methyl 4-amino-3-5-dichloro-6-trifluoromethylpyridine-2-carboxylate (0.16 g, 0.56 mmol) in 5 mL of MeOH was added excess 1N NaOH. The resulting reaction mixture was stirred at room temperature for 1 hr, then made acidic with conc. HCl. The precipitated white solid was collected with suction, washed with $H_2O$ and dried under vacuum to give 80 mg of compound 45: mp 178° C. dec.

26. Preparation of 4-Amino-3-chloro-6-trifluoromethylpyridine-2-carboxylic Acid (Compound 46)

To a solution containing 4-amino-6-trifluoromethylpyridine-2-carboxylic acid methyl ester (0.75 g, 3.4 mmol) in 5 mL of $CH_3CN$ was added dropwise a solution of sulfuryl chloride (0.27 mL, 3.4 mmol) in 1 mL of $CH_3CN$. After stirring at RT for 1 hr, reaction mixture was added to 50 mL of $Et_2O$ and washed with aqueous $NaHCO_3$, dried over $MgSO_4$, filtered and concentrated to give a solid. The crude product was purified by chromatography, eluting with 10% ethyl acetate-hexane to give 200 mg of product as a white solid; mp 131–3° C.

27. Preparation of 4-Amino-3-chloro-6-(3,5-dichlorophenoxy)pyridine-2-carboxylic Acid (Compound 47)

A. Preparation of Methyl 3-Chloro-6-(3,5-dichlorophenoxy)pyridine-2-carboxylate N-oxide To a dry 3-neck round bottom flask was added 60% NaH (0.432 g, 10.81 mmol), dry THF (30 mL) and 3,5-dichlorophenol (1.76 g, 10.81 mmol). The mixture was stirred until evolution of $H_2$ (g) ceased. Methyl 3,6-dichloropyridine-2-carboxylate N-oxide (2.0 g, 9.00 mmol) was added in one portion and stirred at RT for 3 hr, diluted with ethyl acetate and 100 mL of water. The aqueous phase was extracted with ethyl acetate (2×200 mL). The combined extracts were dried ($MgSO_4$) and concentrated to give 2.40 g of white solid.

B. Preparation of Methyl 3,4-Dichloro-6-(3,5-dichlorophenoxy)pyridine-2-carboxylate To Methyl 3-chloro-6-(3,5-dichlorophenoxy)pyridine-2-carboxylic acid N-oxide (2.40 g, 6.89 mmol) dissolved in 50 mL of acetonitrile was added $POC_{13}$ (1.28 mL, 13.77 mmol). The mixture was stirred at reflux overnight after which it was cooled to RT and concentrated to dryness in vacuo. The resultant orange oil was dissolved in diethyl ether and saturated sodium bicarbonate was added carefully. The aqueous phase was extracted with diethyl ether (2×100 mL). The combined organic extracts were dried ($MgSO_4$) and concentrated to dryness. Purification by column chromatography (silica gel) using an eluent of 20% diethyl ether/hexane gave 1.93 g of white solid.

C. Preparation of Methyl 4-Amino-3-chloro-6-(3,5-dichlorophenoxy)pyridine-2-carboxylate Methyl 3,4-dichloro-6-(3,5-dichlorophenoxy)pyridine-2-carboxylic acid (1.93 g, 5.26 mmol) was dissolved in a minimum amount of DMF and to it was carefully added $NaN_3$ (0.444 g, 6.84 mmol) and water to form a homogeneous mixture which was heated to 70° C. and stirred overnight. The reaction mixture was poured into a water-ice mixture and the product was extracted with ethyl acetate (3×100 mL). The combined extracts were washed with pet ether/water (200 mL), dried ($MgSO_4$) and concentrated to dryness in vacuo. The resulting oil was dissolved in methanol and to it was added $NaBH_4$ (0.200 g, 5.26 mmol) and stirred at RT for 1.5 hr. Ethyl acetate and water was added and the aqueous phase was extracted with ethyl acetate (2×100 mL). The combined extracts were dried ($MgSO_4$) and concentrated to dryness. Purification by column chromatography (silica gel) using an eluent of 20% diethyl ether/hexane-50% diethyl ether/hexane to give 0.900 g of clear solid.

D. Preparation of 4-Amino-3-chloro-6-(3,5-dichlorophenoxy)pyridine-2-carboxylic Acid (Compound 47)

To Methyl 4-amino-3-chloro-6-(3,5-dichlorophenoxy) pyridine-2-carboxylic acid (0.0.720 g, 2.07 mmol) in 20 mL of methanol was added 1N NaOH (2.07 mL) and stirred at RT for 1 hr. The reaction mixture was concentrated to dryness in vacuo and 100 mL each of diethyl ether and $H_2O$ added. The aqueous layer acidified with 1N HCl until pH=2. Methylene chloride was added and the aqueous phase was extracted with additional $CH_2Cl_2$ (2×100 mL). The combined extracts were dried ($MgSO_4$) and concentrated to dryness in vacuo to give 0.390 g of white solid 4-amino-3-chloro-6-(3,5-dichlorophenoxy)pyridine-2-carboxylic acid (Compound 47); mp 196° C.

The following 6-phenoxy analogs of 4-amino-3-chloropyridine-2-carboxylic acid were prepared according to the procedure of Example 27:

4-amino-3-chloro-6-phenoxypyridine-2-carboxylic Acid (Compound 48); mp 178° C.

4-amino-3-chloro-6-(4-methoxyphenoxy)pyridine-2-carboxylic Acid (Compound 49); mp 174° C.

4-amino-3-chloro-6-(4-methylphenoxy)pyridine-2-carboxylic Acid (Compound 50); mp 173° C.

4-amino-3-chloro-6-(3,4-dichlorophenoxy)pyridine-2-carboxylic Acid (Compound 51); mp 186–187° C.

4-amino-3-chloro-6-(3-methylphenoxy)pyridine-2-carboxylic Acid (Compound 52); mp 169° C.

4-amino-3-chloro-6-(3-chlorophenoxy)pyridine-2-carboxylic Acid (Compound 53); mp 176° C.

28. Preparation of 4-Amino-3,5-dichloro-6-phenoxypyridine-2-carboxylic Acid (Compound 54)

A. Preparation of Methyl 4-Amino-3,5-dichloro-6-phenoxypyridine-2-carboxylate

A solution of 4-amino-3,5,6-trichloropyridine-2-carboxylic acid (7.2 g, 0.03 mol), phenol (3.0 g, 0.036 mol) and sodium hydroxide (2.7 g 0.068 mol) in DMSO (60 mL) and water (9 mL) was heated to 130° C. for 18 hr. The reaction was diluted with water (250 mL) and a tacky solid collected. This material was dissolved in methanol (100 mL) and treated with $TMSCHN_2$ (25 mL 2M in hexanes). The reaction was stirred 30 min and concentrated. The resulting oil was chromatographed over silica gel (80% hexane and 20% ethyl acetate) to give methyl 4-amino-3,5-dichloro-6-phenoxypyridine-2-carboxylate (1.2, g, 14%); mp 88–90° C.

B. Preparation of 4-Amino-3,5-dichloro-6-phenoxypyridine-2-carboxylic Acid (Compound 54)

To a solution of methyl 4-amino-3,5-dichloro-6-phenoxypyridine-2-carboxylate in methanol (10 mL) and water (100 mL) was added sodium hydroxide (0.5 g excess) and the solution heated under reflux for 3 hr. The solution was cooled and concentrated hydrochloric acid (2 mL) added. The solid was collected to give 4-amino-3,5-dichloro- 6-phenoxypyridine-2-carboxylic acid (1.1 g, 90%); mp 158–60° C.

29. Preparation of 4-Amino-3-chloro-5-fluoro-6-(3,4-dichlorophenoxy)pyridine-2-carboxylic Acid (Compound 55)

4-Amino-3-chloro-6-(3,4-dichlorophenoxy)pyridine-2-carboxylic acid was fluorinated with [1-(chloromethyl)-4-fluoro-1,4-diazoniabicyclo-[2.2.2]octane bis (tetrafluoroborate)] (F-TEDA) in refluxing acetonitrile; mp 156–160° C.

30. Preparation of 4-Amino-3,5-dichloro-6-(2-methylpropoxy)pyridine-2-carboxylic Acid (Compound 56)

4-amino-3,5-dichloro-6-(2-methylpropoxy)pyridine-2-carboxylic Acid (Compound 56) was prepared following the procedure of Example 27 using 2-methylpropanol instead of phenol; mp 104–6° C.

31. Preparation of Herbicidal Compositions

In the following illustrative compositions, parts and percentages are by weight.

EMULSIFIABLE CONCENTRATES

| Formulation A | WT % |
|---|---|
| 4-Amino-3,6-dichloropicolinate, 2-butoxyethyl ester | 26.2 |
| Polyglycol 26-3 Nonionic emulsifier-(di-sec-butyl)phenylpoly(oxypropylene)block polymer with oxyethylene). The polyoxyethelene content is about 12 moles. | 5.2 |
| Witconate P12-20 (Anionic emulsifier-calcium dodecylbenzene sulfonate-60 wt. % active) | 5.2 |
| Aromatic 100 (Xylene range aromatic solvent) | 63.4 |

| Formulation B | WT % |
|---|---|
| 4-Amino-3,6-dichloropicolinate, 2-ethylhexyl ester | 3.5 |
| Sunspray 11N (paraffin oil) | 40.0 |
| Polyglycol 26-3 | 19.0 |
| Oleic acid | 1.0 |
| Xylene range aromatic solvent | 36.5 |

| Formulation C | WT % |
|---|---|
| 4-Amino-3,6-dichloropicolinate, n-butyl ester | 13.2 |
| Stepon C-65 | 25.7 |
| Ethomeen T/25 | 7.7 |
| Ethomeen T/15 | 18.0 |
| Xylene range aromatic solvent | 35.4 |

These concentrates can be diluted with water to give emulsions of suitable concentrations for controlling weeds.

WETTABLE POWDERS

| Formulation D | WT % |
|---|---|
| 4-Amino-3,6-dichloropicolinic acid | 26.0 |
| Polyglycol 26-3 | 2.0 |
| Polyfon H | 4.0 |
| Zeosyl 100 (Precipitated hydrated $SiO_2$) | 17.0 |
| Barden clay + inerts | 51.0 |

| Formulation E | WT % |
|---|---|
| 4-Amino-3,6-dichloropicolinic acid | 62.4 |
| Polyfon H (sodium salt of lignin sulfonate) | 6.0 |
| Sellogen HR (sodium naphthalene sulfonate) | 4.0 |
| Zeosyl 100 | 27.6 |

The active ingredient is applied to the corresponding carriers and then these are mixed and ground to yield wettable powders of excellent wettability and suspension power. By diluting these wettable powders with water it is possible to obtain suspensions of suitable concentrations for controlling weeds.

WATER DISPERSIBLE GRANULES

| Formulation F | WT % |
|---|---|
| 4-Amino-3,6-dichloropicolinic acid | 26.0 |
| Sellogen HR | 4.0 |
| Polyfon H | 5.0 |
| Zeosyl 100 | 17.0 |
| Kaolinite clay | 48.0 |

The active ingredient is added to the hydrated silica, which is then mixed with the other ingredients and ground to a powder. The powder is agglomerated with water and sieved to provide granules in the range of −10 to +60 mesh. By dispersing these granules in water it is possible to obtain suspensions of suitable concentrations for controlling weeds.

GRANULES

| Formulation G | WT % |
|---|---|
| 4-Amino-3,6-dichloropicolinic acid | 5.0 |
| Celetom MP-88 | 95.0 |

The active ingredient is applied in a polar solvent such as N-methyl-pyrollidinone, cyclohexanone, gammabutyrolactone, etc. to the Celetom MP 88 carrier or to other suitable carriers. The resulting granules can be applied by hand, granule applicator, airplane, etc. in order to control weeds.

| Formulation H | WT % |
|---|---|
| 4-Amino-3,6-dichloropicolinic acid | 1.0 |
| Polyfon H | 8.0 |
| Nekal BA 77 | 2.0 |
| Zinc Stearate | 2.0 |
| Barden Clay | 87.0 |

All materials are blended and ground to a powder then water is added and the clay mixture is stirred until a paste is formed. The mixture is extruded through a die to provide granules of proper size.

Water Soluble Liquids

| Formulation I | Wt % |
|---|---|
| 4-Amino-3,6-dichloropicolinic acid | 11.2 |
| KOH | 3.7 |
| Water | 85.1 |

4-Amino-3,6-dichloropicolinic acid is dispersed in water. KOH is slowly added to neutralize the acid to a pH of between 9–12. A water-soluble surfactant may be added. Other aids may be incorporated to improve physical, chemical and/or formulation properties.

32. Evaluation of Postemergence Herbicidal Activity

Seeds of the desired test plant species were planted in Grace-Sierra MetroMix® 306 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7–21 days in a greenhouse with an approximate 15 hr photoperiod which was maintained at about 23–29° C. during the day and 22–28° C. during the night. Nutrients and water were added on a regular basis and supplemental lighting was provided with overhead metal halide 1000-Watt lamps as necessary. The plants were employed for testing when they reached the first or second true leaf stage.

A weighed amount, determined by the highest rate to be tested, of each test compound was placed in a 20 mL glass vial and was dissolved in 4 mL of a 97:3 v/v (volume/volume) mixture of acetone and dimethyl sulfoxide (DMSO) to obtain concentrated stock solutions. If the test compound did not dissolve readily, the mixture was warmed and/or sonicated. The concentrated stock solutions obtained were diluted with an aqueous mixture containing acetone, water, isopropyl alcohol, DMSO, Atplus 411F crop oil concentrate, and Triton X-155 surfactant in a 48.5:39:10:1.5:1.0:0.02 v/v ratio to obtain spray solutions of known concentration. The solutions containing the highest concentration to be tested were prepared by diluting 2 mL aliquots of the stock solution with 13 mL of the mixture and lower concentrations were prepared by serial dilution of the stock solution. Approximately 1.5 mL aliquots of each solution of known concentration were sprayed evenly onto each of the test plant pots using a Devilbiss atomizer driven by compressed air pressure of 2 to 4 psi (140 to 280 kilopascals) to obtain thorough coverage of each plant. Control plants were sprayed in the same manner with the aqueous mixture. In this test an application rate of 1 ppm results in the application of approximately 1 g/Ha.

The treated plants and control plants were placed in a greenhouse as described above and watered by sub-irrigation to prevent wash-off of the test compounds. After 2 weeks the condition of the test plants as compared with that of the untreated plants was determined visually and scored on a scale of 0 to 100 percent where 0 corresponds to no injury and 100 corresponds to complete kill.

By applying the well-accepted probit analysis as described by J. Berkson in *Journal of the American Statistical Society*, 48, 565 (1953) and by D. Finney in "*Probit Analysis*" Cambridge University Press (1952), the above data can be used to calculate $GR_{50}$ and $GR_{80}$ values, which are defined as growth reduction factors that correspond to the effective dose of herbicide required to kill or control 50 percent or 80 percent, respectively, of a target plant.

Some of the compounds tested, application rates employed, plant species tested, and results are given in Tables 1–2. Selectivity to rice, corn and wheat are illustrated in Tables 3–5.

TABLE 1

Post-emergent % Control

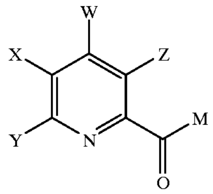

| # | M | W | X | Y | Z | % Control XANST | STEME | POLCO | Rate (ppm) |
|---|---|---|---|---|---|---|---|---|---|
| 1 | OH | $NH_2$ | H | Cl | Cl | 95 | 100 | 100 | 125 |
| 2 | O-2-EH[2] | $NH_2$ | H | Cl | Cl | 95 | 80 | 100 | 250 |
| 3 | O—Me | $NH_2$ | H | Cl | Cl | 100 | 100 | 100 | 125 |
| 4 | O—Et | $NH_2$ | H | Cl | Cl | 100 | 100 | 100 | 125 |
| 5 | O—Pr | $NH_2$ | H | Cl | Cl | 100 | 100 | 100 | 125 |
| 6 | O-i-Pr | $NH_2$ | H | Cl | Cl | 100 | 100 | 100 | 125 |
| 7 | O—Bu | $NH_2$ | H | Cl | Cl | 100 | 100 | 100 | 250 |
| 8 | O-pentyl | $NH_2$ | H | Cl | Cl | 100 | 90 | 100 | 250 |
| 9 | O-hexyl | $NH_2$ | H | Cl | Cl | 100 | 100 | 100 | 250 |
| 10 | O—BE[3] | $NH_2$ | H | Cl | Cl | 90 | 50 | 100 | 125 |
| 11 | $NH_2$ | $NH_2$ | H | Cl | Cl | 80 | 85 | 95 | 125 |
| 12 | O—Me | NHC(O)Me | H | Cl | Cl | 90 | 30 | 100 | 125 |
| 13 | O—Me | $N(C(O)Me)_2$ | H | Cl | Cl | 95 | 100 | 80 | 250 |
| 14 | OH | $NH_2$ | H | Br | Cl | 85 | 90 | 50 | 250 |
| 15 | OH | $NH_2$ | H | F | Cl | 100 | 70 | 90 | 250 |
| 16 | OH | $NH_2$ | F | Br | F | 60 | 30 | 70 | 250 |
| 17 | OH | $NH_2$ | H | Br | Br | 100 | 80 | 100 | 250 |
| 18 | O—Me | $NH_2$ | Br | Br | Br | 85 | 90 | 75 | 250 |
| 19 | OH | $NH_2$ | F | Cl | Cl | 95 | 95 | 100 | 125 |
| 20 | OH | $NH_2$ | Br | Cl | Cl | 85 | 90 | 50 | 250 |
| 21 | OH | $NH_2$ | $CF_3$ | Cl | Cl | 70 | 20 | 20 | 250 |
| 22 | OH | $NH_2$ | O—Me | Cl | Cl | 80 | 90 | 100 | 250 |
| 23 | OH | $NH_2$ | S—Et | Cl | Cl | 90 | 90 | 98 | 125 |
| 24 | OH | $NH_2$ | S—Ph | Cl | Cl | 60 | 50 | 50 | 250 |
| 25 | O—Me | $NH_2$ | $NO_2$ | Cl | Cl | 60 | 50 | 50 | 250 |
| 26 | OH | NHMe | H | Cl | Cl | 90 | 90 | 95 | 125 |
| 27 | OH | NHEt | H | Cl | Cl | 85 | 100 | 90 | 125 |
| 28 | OH | NH-i-Pr | H | Cl | Cl | 95 | 90 | 95 | 250 |
| 29 | OH | NHBu | H | Cl | Cl | 95 | 90 | 90 | 250 |
| 30 | OH | NH(allyl) | H | Cl | Cl | 100 | 80 | 100 | 250 |
| 31 | OH | $NH(CH_2)_2OH$ | Cl | Cl | Cl | 40 | 30 | 70 | 250 |
| 32 | OH | $NH(CH_2)_2OMe$ | H | Cl | Cl | 80 | 20 | 100 | 250 |
| 33 | OH | $NMe_2$ | H | Cl | Cl | 100 | 100 | 100 | 250 |
| 34 | OH | NMe(OH) | H | Cl | Cl | 100 | 70 | 100 | 125 |
| 35 | OH | NMe(OMe) | H | Cl | Cl | 90 | 60 | 100 | 125 |
| 36 | OH | pyrrolidine | H | Cl | Cl | 50 | 40 | 80 | 125 |
| 37 | OH | pyrrole | H | Cl | Cl | 90 | 70 | 90 | 125 |
| 38 | O—Me | $N_3$ | H | Br | Cl | 90 | 50 | 90 | 125 |

TABLE 1-continued

Post-emergent % Control

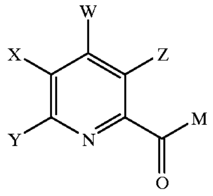

| # | M | W | X | Y | Z | % Control XANST | STEME | POLCO | Rate (ppm) |
|---|---|---|---|---|---|---|---|---|---|
| 39[1] | OH | $NO_2$ | H | Cl | Cl | 85 | 30 | 90 | 125 |
| 40 | OH | N═CH(NMe$_2$) | H | Cl | Cl | 100 | 90 | 100 | 250 |
| 41 | OH | $NH_2$ | H | Br | O—Me | 80 | 90 | 100 | 125 |
| 42 | OH | $NH_2$ | Cl | Br | O—Me | 85 | 90 | 90 | 250 |
| 43 | OH | $NH_2$ | Cl | Cl | F | 90 | 85 | 60 | 125 |
| 44 | OH | $NH_2$ | H | Cl | Br | 90 | 90 | 95 | 125 |
| 45 | O—Me | $NH_2$ | Cl | $CF_3$ | Cl | 90 | 0 | 80 | 250 |
| 46 | O—Me | $NH_2$ | H | $CF_3$ | Cl | 90 | 60 | 100 | 250 |
| 47 | OH | $NH_2$ | H | O-3,5-DCPh[4] | Cl | 100 | 100 | 100 | 250 |
| 48 | OH | $NH_2$ | H | O—Ph | Cl | 100 | 60 | 100 | 250 |
| 49 | OH | $NH_2$ | H | O-4-MeOPh[5] | Cl | 60 | 0 | 70 | 250 |
| 50 | OH | $NH_2$ | H | O-4-MePh[6] | Cl | 60 | 0 | 70 | 250 |
| 51 | OH | $NH_2$ | H | O-3,4-DCPh[7] | Cl | 100 | 70 | 100 | 250 |
| 52 | OH | $NH_2$ | H | O-3-MePh[8] | Cl | 70 | 20 | 90 | 250 |
| 53 | OH | $NH_2$ | H | O-3-CPh[9] | Cl | 100 | 100 | 100 | 250 |
| 54 | OH | $NH_2$ | Cl | O—Ph | Cl | 100 | 0 | 40 | 250 |
| 55 | OH | $NH_2$ | F | O-3,4-DCPh[7] | Cl | 100 | 95 | 100 | 250 |
| 56 | OH | $NH_2$ | Cl | O-2-MP[10] | Cl | 85 | 30 | 20 | 250 |

[1]Compound 39 is the pyridine N-oxide
[2]O-2—EH = O-2-ethylhexyl
[3]O—BE = O—$(CH_2)_2$OBu
[4]O-3,5-DCPh = O-3,5-Dichloro$C_6H_3$
[5]O-5-MeOPh = O-4-Methoxy$C_6H_4$
[6]O-4-MePh = O-4-Methyl$C_6H_4$
[7]O-3,4-DCPh = O-3,4-Dichloro$C_6H_3$
[8]O-3-MePh = O-3-Methyl$C_6H_4$
[9]O-3-CPh = O-3-Chloro$C_6H_4$
[10]O-2-MP = O-2-Methylpropyl
NT = not tested
XANST = cocklebur (*Xanthium strumarium*)
STEME = chickweed (*Stellaria media*)
POLCO = wild buckwheat (*Polygonum convolvulus*)

TABLE 2

POSTMERGENCE HERBICIDAL ACTIVITY % CONTROL

| Cpd. No. | Rate, ppm | STEME | XANST | CHEAL | AMARE | ABUTH | VIOTR | POLCO | ALOMY | ECHCG | DIGSA | SETFA | SORBI | AVEFA |
|---|---|---|---|---|---|---|---|---|---|---|---|---|---|---|
| 1 | 125 | 90 | 100 | 100 | 95 | 70 | 80 | 100 | 50 | 45 | 60 | 75 | 50 | 50 |
| 4 | 125 | 70 | 100 | 100 | 100 | 70 | 70 | 100 | 40 | 50 | 70 | 75 | 40 | 40 |
| 14 | 125 | 65 | 100 | 95 | 90 | 85 | 75 | 100 | 50 | 65 | 65 | 65 | 60 | 40 |
| 19 | 125 | 60 | 95 | 95 | 60 | 50 | 50 | 100 | 20 | 10 | 30 | 20 | 10 | 20 |

STEME = chickweed (*Stellaria media*)
CHEAL = lambsquarters (*Chenopodium album*)
ABUTH = velvetleaf (*Abutilion theophrasti*)
POLCO = wild buckwheat (*Polygonum convolvulus*)
ECHCG = barnyardgrass (*Echinochloa crus-galli*)
SETFA = giant foxtail (*Setaria faberi*)
AVEFA = wild oats (*Avena fatua*)
XANST = cocklebur (*Xanthium strumarium*)
AMARE = pigweed (*Amaranthus retroflexus*)
VIOTR = viola (*Viola tricolor*)
ALOMY = blackgrass (*Alopecurus myosuroides*)
DIGSA = crabgrass (*Digitaria sanguinalis*)
SORBI = Rox orange sorghum (Sorghum bicolor)

TABLE 3

Control of Several Key Weeds in Rice
post emergent evaluation - % control

| cmpd # | ORYZA | ECHCG | CYPES | Rate (ppm) |
|---|---|---|---|---|
| 1 | 10 | 75 | 75 | 250 |
| 14 | 10 | 65 | 75 | 250 |
| 27 | 40 | 70 | 50 | 250 |

ORYZA = rice (*Oryza sativa*)
ECHCG = Barnyardgrass (*Echinochloa crus-galli*)
CYPES = yellow nutsedge (*Cyperus esculentus*)

TABLE 4

Control of Several Key Weeds in Corn
Post-emergent Evaluation - % control

| cmpd # | ZEAMX | ABUTH | AMARE | XANST | Rate (ppm) |
|---|---|---|---|---|---|
| 15 | 0 | 40 | 75 | 90 | 250 |
| 20 | 10 | 70 | 90 | 85 | 250 |
| 33 | 20 | 80 | 50 | 100 | 125 |
| 43 | 0 | 70 | 90 | 85 | 250 |

ZEAMX = corn (*Zea mays*)
ABUTH = velvetleaf (*Abutilion theophrasti*)
AMARE = pigweed (*Amaranthus retroflexus*)
XANST = cocklebur (*Xanthium strumarium*)

TABLE 5

Control of Several Key Weeds in Wheat
Post-emergent Evaluation - % control

| cmpd # | TRZAS | STEME | CHEAL | POLCO | Rate (ppm) |
|---|---|---|---|---|---|
| 14 | 0 | 70 | 70 | 90 | 250 |
| 23 | 20 | 30 | 90 | 98 | 125 |
| 41 | 10 | 20 | 90 | 100 | 250 |
| 46 | 10 | 50 | 100 | 100 | 31 |

TRZAS = wheat (*Triticum aestivum*)
STEME = chickweed (*Stellaria media*)
CHEAL = lambsquarters (*Chenopodiuin album*)
POLCO = wild buckwheat (*Polygonum convolvulus*)

3. Evaluation of Preemergence Herbicidal Activity

Seeds of the desired test plant species were planted in a soil matrix prepared by mixing a loam soil (43 percent silt, 19 percent clay, and 38 percent sand, with a pH of about 8.1 and an organic matter content of about 1.5 percent) and sand in a 70 to 30 ratio. The soil matrix was contained in plastic pots with a surface area of 113 square centimeters. When required to ensure good germination and healthy plants, a fungicide treatment and/or other chemical or physical treatment was applied.

A weighed amount, determined by the highest rate to be tested, of each test compound was placed in a 20 ml glass vial and was dissolved in 4 mL of a 97:3 v/v (volume/volume) mixture of acetone and dimethyl sulfoxide to obtain concentrated stock solutions. If the test compound did not dissolve readily, the mixture was warmed and/or sonicated. The stock solutions obtained were diluted with a 99.9:0.1 mixture of water and Tween® 155 surfactant to obtain application solutions of known concentration. The solutions containing the highest concentration to be tested were prepared by diluting 2 mL aliquots of the stock solution with 15 mL of the mixture and lower concentrations were prepared by serial dilution of the stock solution. A 2.5 mL aliquot of each solution of known concentration was sprayed evenly onto the soil surface (113 sq. cm) of each seeded pot using a Cornwall 5.0 mL glass syringe fitted with a TeeJet TN-3 hollow cone nozzle to obtain thorough coverage of the soil in each pot. Control pots were sprayed in the same manner with the aqueous mixture.

The treated pots and control pots were placed in a greenhouse maintained with an approximate 15 hr photoperiod and temperatures of about 23–29° C. during the day and 22–28° C. during the night. Nutrients and water were added on a regular basis and supplemental lighting was provided with overhead metal halide 1000-Watt lamps as necessary. The water was added by top-irrigation. After 3 weeks the condition of the test plants that germinated and grew as compared with that of the untreated plants that germinated and grew was determined visually and scored on a scale of 0 to 100 percent where 0 corresponds to no injury and 100 corresponds to complete kill or no germination. Some of the compounds tested, application rates employed, plant species tested, and results are given in Tables 6–7.

TABLE 6

Pre-emergent % Control

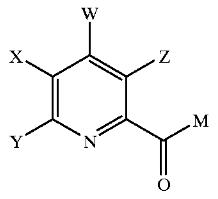

| # | M | W | X | Y | Z | % Control IPOHE | AMARE | ABUTH | Rate (ppm) |
|---|---|---|---|---|---|---|---|---|---|
| 1 | OH | $NH_2$ | H | Cl | Cl | 100 | 100 | 100 | 280 |
| 2 | O-2-EH[2] | $NH_2$ | H | Cl | Cl | 100 | 100 | 100 | 280 |
| 3 | O—Me | $NH_2$ | H | Cl | Cl | 100 | 100 | 100 | 280 |
| 4 | O—Et | $NH_2$ | H | Cl | Cl | 100 | 100 | 100 | 280 |
| 5 | O—Pr | $NH_2$ | H | Cl | Cl | 100 | 100 | 100 | 280 |

TABLE 6-continued

Pre-emergent % Control

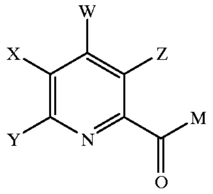

| # | M | W | X | Y | Z | % Control | | | Rate (ppm) |
|---|---|---|---|---|---|---|---|---|---|
| | | | | | | IPOHE | AMARE | ABUTH | |
| 6 | O-i-Pr | $NH_2$ | H | Cl | Cl | 100 | 100 | 100 | 280 |
| 7 | O—Bu | $NH_2$ | H | Cl | Cl | 100 | 100 | 100 | 280 |
| 8 | O-pentyl | $NH_2$ | H | Cl | Cl | 100 | 100 | 100 | 280 |
| 9 | O-hexyl | $NH_2$ | H | Cl | Cl | 100 | 98 | 100 | 280 |
| 10 | O—BE[3] | $NH_2$ | H | Cl | Cl | 100 | 100 | 100 | 280 |
| 11 | $NH_2$ | $NH_2$ | H | Cl | Cl | 85 | 0 | 85 | 560 |
| 12 | O—Me | NHC(O)Me | H | Cl | Cl | 100 | 100 | 95 | 560 |
| 13 | O—Me | $N(C(O)Me)_2$ | H | Cl | Cl | 95 | 100 | 95 | 560 |
| 14 | OH | $NH_2$ | H | Br | Cl | 100 | 90 | 100 | 560 |
| 15 | OH | $NH_2$ | H | F | Cl | 100 | 100 | 100 | 560 |
| 16 | OH | $NH_2$ | F | Br | F | 80 | 70 | 0 | 560 |
| 17 | OH | $NH_2$ | H | Br | Br | 100 | 100 | 100 | 560 |
| 18 | O—Me | $NH_2$ | Br | Br | Br | 30 | 80 | 98 | 280 |
| 19 | OH | $NH_2$ | F | Cl | Cl | 100 | 100 | 100 | 560 |
| 20 | OH | $NH_2$ | Br | Cl | Cl | 100 | 100 | 100 | 560 |
| 21 | OH | $NH_2$ | $CF_3$ | Cl | Cl | 90 | 80 | 80 | 560 |
| 22 | OH | $NH_2$ | O—Me | Cl | Cl | 100 | 100 | 100 | 560 |
| 23 | OH | $NH_2$ | S—Et | Cl | Cl | 0 | 40 | 40 | 560 |
| 24 | OH | $NH_2$ | S—Ph | Cl | Cl | 30 | 20 | 50 | 560 |
| 25 | O—Me | $NH_2$ | $NO_2$ | Cl | Cl | nt | nt | nt | 250 |
| 26 | OH | NHMe | H | Cl | Cl | 100 | 100 | 100 | 560 |
| 27 | OH | NHEt | H | Cl | Cl | 100 | 100 | 100 | 560 |
| 28 | OH | NH-i-Pr | H | Cl | Cl | 100 | 100 | 100 | 560 |
| 29 | OH | NHBu | H | Cl | Cl | 100 | 100 | 100 | 560 |
| 30 | OH | NH(allyl) | H | Cl | Cl | 85 | 90 | 95 | 560 |
| 31 | OH | $NH(CH_2)_2OH$ | Cl | Cl | Cl | 100 | 95 | 95 | 560 |
| 32 | OH | $NH(CH_2)_2OMe$ | H | Cl | Cl | 90 | 70 | 90 | 560 |
| 33 | OH | $NMe_2$ | H | Cl | Cl | 100 | 100 | 98 | 560 |
| 34 | OH | NMe(OH) | H | Cl | Cl | 95 | 100 | 100 | 560 |
| 35 | OH | NMe(OMe) | H | Cl | Cl | 85 | 95 | 90 | 560 |
| 36 | OH | pyrrolidine | H | Cl | Cl | 80 | 80 | 95 | 560 |
| 37 | OH | pyrrole | H | Cl | Cl | 95 | 100 | 100 | 560 |
| 38 | O—Me | $N_3$ | H | Br | Cl | 100 | 100 | 100 | 560 |
| 39[1] | OH | $NO_2$ | H | Cl | Cl | 100 | 100 | 100 | 560 |
| 40 | OH | $N{=}CH(NMe_2)$ | H | Cl | Cl | 100 | 100 | 100 | 560 |
| 41 | OH | $NH_2$ | H | Br | O—Me | 85 | 40 | 90 | 280 |
| 42 | OH | $NH_2$ | Cl | Br | O—Me | 100 | 100 | 100 | 560 |
| 43 | OH | $NH_2$ | Cl | Cl | F | 70 | 30 | 80 | 140 |
| 44 | OH | $NH_2$ | H | Cl | Br | 100 | 100 | 100 | 560 |
| 45 | O—Me | $NH_2$ | Cl | $CF_3$ | Cl | 100 | 100 | 90 | 125 |
| 46 | O—Me | $NH_2$ | H | $CF_3$ | Cl | 100 | 95 | 95 | 140 |
| 47 | OH | $NH_2$ | H | O-3,5-DCPh[4] | Cl | 0 | 100 | 95 | 280 |
| 48 | OH | $NH_2$ | H | O—Ph | Cl | 100 | 30 | 100 | 280 |
| 49 | OH | $NH_2$ | H | O-4-MeOPh[5] | Cl | 0 | 0 | 0 | 70 |
| 50 | OH | $NH_2$ | H | O-4-MePh[6] | Cl | 0 | 0 | 0 | 70 |
| 51 | OH | $NH_2$ | H | O-3,4-DCPh[7] | Cl | 0 | 98 | 80 | 280 |
| 52 | OH | $NH_2$ | H | O-3-MePh[8] | Cl | 70 | 20 | 50 | 560 |
| 53 | OH | $NH_2$ | H | O-3-CPh[9] | Cl | 100 | 0 | 100 | 560 |
| 54 | OH | $NH_2$ | Cl | O—Ph | Cl | 41 | 10 | 50 | 280 |
| 55 | OH | $NH_2$ | F | O-3,4-DCPh[7] | Cl | 100 | 95 | 100 | 250 |
| 56 | OH | $NH_2$ | Cl | O-2-MP[10] | Cl | 0 | 0 | 40 | 560 |

[1]Compound 39 is the pyridine N-oxide
[2]O-2-EH = O-2-ethylhexyl
[3]O—BE = O—$(CH_2)_2$OBu
[4]O-3,5-DCPh = O-3,5-Dichloro$C_6H_3$
[5]O-4-MeOPh = O-4-Methoxy$C_6H_4$
[6]O-4-MePh = O-4-Methyl$C_6H_4$
[7]O-3,4-DCPh = O-3,4-Dichloro$C_6H_3$
[8]O-3-MePh = O-3-Methyl$C_6H_4$
[9]O-3-CPh = O-3-Chloro$C_6H_4$
[10]O-2-MP = O-2-Methylpropyl TABLE 6-continued Pre-emergent % Control

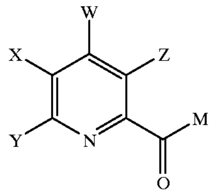

| # | M | W | X | Y | Z | % Control IPOHE | AMARE | ABUTH | Rate (ppm) |
|---|---|---|---|---|---|---|---|---|---|

NT = not tested
IPOHE = morningglory (*Ipomoea hederacea*)
AMARE = pigweed (*Amaranthus retroflexus*)
ABUTH = velvetleaf (*Abutilon theophrasti*)

TABLE 7

PREEMERGENCE HERBICIDAL ACTIVITY % CONTROL

| Cpd. No. | Rate, g/Ha | XANST | CHEAL | AMARE | ABUTH | EPHHL | ALOMY | ECHCG | DIGSA | SETFA | SORBI | AVEFA |
|---|---|---|---|---|---|---|---|---|---|---|---|---|
| 1 | 35 | 99 | 99 | 88 | 95 | 62 | 36 | 17 | 20 | 40 | 60 | 37 |
| 3 | 35 | 90 | 100 | 90 | 95 | 20 | nt | 20 | 40 | 40 | 30 | 10 |
| 14 | 35 | 100 | 100 | 100 | 100 | 70 | 60 | 40 | 80 | 98 | 50 | 40 |
| 42 | 35 | 98 | 90 | 60 | 80 | 40 | 30 | 30 | 30 | 30 | 20 | 30 |

nt = no test
XANST = cocklebur (*Xanthium strumarium*)
ABUTH = velvetleaf (*Abutilion theophrasti*)
ALOMY = blackgrass (*Alopecurus myosuroides*)
DIGSA = crabgrass (*Digitaria sanguinalis*)
SORBI = Rox orange sorghum (Sorghum bicolor)
CHEAL = lambsquarters (*Chenopodium album*)
AMARE = pigweed (*Amaranthus retroflexus*)
EPHHL = wild poinsettia (*Euphorbia heterophylla*)
ECHCG = barnyardgrass (*Echinochloa crus-galli*)
SEFTA = giant foxtail (*Setaria faberi*)
AVEFA = wild oats (*Avena fatua*)

34. Range & Pasture Crop Testing

Rates a re calculated based upon 5 doses being applied. The high rate (X), followed by serial dilutions of ½X, ¼X, ⅛X and 1/16X. Compound requirements are based upon the 187 Liha carrier volume, specifications of the delivery system (Mandel track sprayer) and genera ting 24 mL of technical spray material to allow for the dilutions and overage in the sprayer.

$$\frac{\text{Rate g/ha}}{\text{187 L/ha}} = \frac{\text{X mg}}{\text{24 mL}}$$

| Example: | Starting X rate (g/ha) | mgs required |
|---|---|---|
| | 560 | 71.9 |
| | 280 | 35.9 |
| | 140 | 17.95 |
| | 70 | 8.9 |

All technical materials were formulated in 97:3 (acetone:DMSO) with 0.25% X-77. The total volume of solvent is maintained at less than 7%. An overhead Mandel track sprayer calibrated to deliver 187 Lhai was used for all treatment applications (post-merged). Pillar was included as a comparison treatment.

Solutions were applied with a mechanized track-sprayer at the following settings:

Nozzle: 8002E

Speed: 2 mph

Spray Pressure: 40 psi

Spray height: 17 inches above top of plants

This provides an application volume of 187 L/ha

Percent weed control (burn down) was evaluated 3 weeks after treatment. Visual control on a 0–100 linear scale was used, with 0 representing no control and 100 representing total control. Burn down ratings were taken for annual and perennial weed species Some of the compounds tested, application rates employed, plant species tested, and results are given in Tables 8–10.

TABLE 8

| | Salts of Compound 1 | | |
|---|---|---|---|
| | Post-emergent $GR_{80}$ g/Ha | | |
| salt | CASOB | CONAR | CIRAR |
| free acid | 11 | 59 | 47 |
| potassium salt | <8.8 | 36 | 27 |
| amine salt | <8.8 | 34 | 37 |
| dimethylamine salt | 11.8 | >140 | 43 |
| monoethanolamine salt | 11 | 20 | 18 |
| triethylamine salt | <8.8 | 16 | <8.8 |
| triisopropanolamine salt | 11 | 20 | 43 |

CASOB = sicklepod (*Cassia obtusifolia*)
CONAR = field bindweed (*Convolvulus arvensis*)
CIRAR = Canada thistle (*Cirsium arvense*), 3 week evaluation

TABLE 9

Control of Several Key Weeds in Pasture Post-emergent Evaluation - % control

| Cmpd # | AGRCR | CIRAR | RUMOB | AMBEL | Rate (g/Ha) |
|---|---|---|---|---|---|
| 3 | 30 | 90 | 100 | 100 | 70 |
| 6 | 30 | 95 | 100 | 93 | 70 |
| 26 | 10 | 90 | 100 | nt | 70 |
| 23 | 30 | 80 | 100 | 85 | 70 |

AGRCR = crested wheatgrass (*Agropyron cristatum) (grass crop)*
CIRAR = Canada thistle (*Cirsium arvense*)
RUMOB = broadleaf dock (*Rumex obtusifolia*)
AMBEL = common ragweed (*Ambrosia artemisiifolia*)
3 week evaluation
nt = not tested

TABLE 10

Control of Several Key Weeds in Clover Pasture

| | | g/ha | |
|---|---|---|---|
| Cmpd | $GR_{20}$ TRFRE | $GR_{80}$ CONAR | $GR_{80}$ CIRAR |
| 3 | <17.5 | 127.7 | <17.5 |
| 4 | <17.5 | 59 | <17.5 |
| 5 | <17.5 | 140.1 | <17.5 |
| 6 | 98.8 | 98.8 | <17.5 |
| 7 | 15.3 | 116.6 | 17.3 |
| 9 | 20.7 | 66 | 20.7 |

TRFRE = White Clover (*Trifolium repens*)
CONAR = Field Bindweed (*Convolvulus arvensis*)
CIRAR = Canada thistle (*Cirsium arvense*)

What is claimed is:

1. A compound of Formula I:

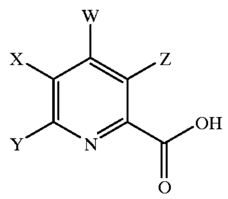

I wherein

X represents H, halogen, $C_1$–$C_6$ alkoxy, $C_1$–$C_6$ alkylthio, aryloxy, nitro, or trifluoromethyl;

Y represents halogen, $C_1$–$C_6$ alkoxy, $C_1$–$C_6$ alkylthio, aryloxy, heteroaryloxy or trifluoromethyl;

Z represents halogen, $C_1$–$C_6$ alkoxy, $C_1$–$C_6$ alkylthio, aryloxy or nitro; and W represents —$NO_2$, —$N_3$, —$NR_1R_2$, —N═$CR_3R_4$ or —NHN═$CR_3R_4$ where $R_1$ and $R_2$ independently represent H, $C_1$–$C_6$ alkyl, $C_3$–$C_6$ alkenyl, $C_3$–$C_6$ alkynyl, aryl, heteroaryl, hydroxy, $C_1$–$C_6$ alkoxy, amino, $C_1$–$C_6$ acyl, $C_1$–$C_6$ carboalkoxy, $C_1$–$C_6$ alkylcarbamyl, $C_1$–$C_6$ alkylsulfonyl, $C_1$–$C_6$ trialkylsilyl or $C_1$–$C_6$ dialkyl phosphonyl or $R_1$ and $R_2$ taken together with N represent a 5- or 6-membered saturated or unsaturated ring which may contain additional O, S or N heteroatoms; and $R_3$ and $R_4$ independently represent H, $C_1$–$C_6$ alkyl, $C_3$–$C_6$ alkenyl, $C_3$–$C_6$ alkynyl, aryl or heteroaryl or $R_3$ and $R_4$ taken together with ═C represent a 5- or 6-membered saturated ring; and agriculturally acceptable derivatives of the carboxylic acid, with the proviso that 1) when X represents H or Cl, then Y and Z are not both Cl and 2) when X and Z both represent Cl, then Y is not Br.

2. A compound of claim 1 wherein:

X represents H, halogen, or trifluoromethyl;

Y represents halogen, aryloxy, heteroaryloxy, or trifluoromethyl;

Z represents halogen; and

W represents —$NR_1R_2$ where $R_1$ and $R_2$ independently represent H, $C_1$–$C_6$ alkyl, $C_3$–$C_6$ alkenyl, $C_3$–$C_6$ alkynyl or $R_1$ and $R_2$ taken together with N represent a 5- or 6-membered saturated ring which may contain additional O or N heteroatoms; and agriculturally acceptable salts, esters or amides of the carboxylic acid.

3. A compound of claim 1 wherein:

X represents H or F;

Y represents F, Cl, Br or aryloxy;

Z represents Cl; and

W represents —$NH_2$.

4. A compound of claim 1 wherein:

Y represents a phenoxy group substituted with halogen or $C_1$–$C_4$ alkyl groups in the 3-position.

5. A n herbicidal composition comprising an herbicidally effective amount of a 4-aminopicolinate of Formula I:

I

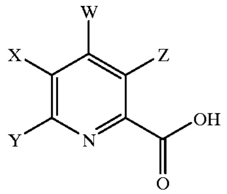

wherein

X represents H, halogen, $C_1$–$C_6$ alkoxy, $C_2$–$C_6$ alkylthio, aryloxy, nitro or trifluoromethyl;

Y represents halogen, $C_1$–$C_6$ alkoxy, $C_1$–$C_6$ alkylthio, aryloxy, heteroaryloxy or trifluoromethyl;

Z represents halogen, $C_1$–$C_6$ alkoxy, $C_1$–$C_6$ alkylthio aryloxy or nitro; and W represents —$NO_2$, —$N_3$, —$NR_1R_2$, —N═$CR_3R_4$ or —NHN═$CR_3R_4$ where $R_1$ and $R_2$ independently represent H, $C_1$–$C_6$ alkyl, $C_3$–$C_6$ alkenyl, $C_3$–$C_6$ alkynyl, aryl, heteroaryl, hydroxy, $C_1$–$C_6$ alkoxy, amino, $C_1$–$C_6$ acyl, $C_1$–$C_6$ carboalkoxy, $C_1$–$C_6$ alkylcarbamyl, $C_1$–$C_6$ alkylsulfonyl, $C_1$–$C_6$ trialkylsilyl or $C_1$–$C_6$ dialkyl phosphonyl or $R_1$ and $R_2$ taken together with N represent a 5- or 6-membered saturated or unsaturated ring which may contain additional O, S or N heteroatoms; and $R_3$ and $R_4$ independently represent H, $C_1$–$C_6$ alkyl, $C_3$–$C_6$ alkenyl, $C_3$–$C_6$ alkynyl, aryl or heteroaryl or $R_3$ and $R_4$ taken together with ═C represent a 5- or 6-membered saturated ring; and agriculturally acceptable derivatives of the carboxylic acid, with the proviso that when X represents Cl, then Y and Z are not both Cl, in admixture with an agriculturally acceptable adjuvant or carrier.

6. An herbicidal composition of claim 5 wherein:

X represents H, halogen or trifluoromethyl;

Y represents halogen, aryloxy, heteroaryloxy or trifluoromethyl;

Z represents halogen; and

W represents —$NR_1R_2$ where $R_1$ and $R_2$ independently represent H, $C_1$–$C_6$ alkyl, $C_3$–$C_6$ alkenyl, $C_3$–$C_6$ alkynyl or $R_1$ and $R_2$ taken together with N represent a 5- or 6-membered saturated ring which may contain additional O or N heteroatoms; and agriculturally acceptable salts, esters or amides of the carboxylic acid.

7. An herbicidal composition of claim 5 wherein:

X represents H or F;

Y represents F, Cl, Br or aryloxy;

Z represents Cl; and

W represents —$NH_2$.

8. An herbicidal composition of claim 5 wherein:

Y represents a phenoxy group substituted with halogen or $C_1$–$C_4$ alkyl groups in the 3-position.

9. An herbicidal composition of claim 5 containing 4-amino-3,6-dichloropyridine-2-carboxylic acid or an agriculturally acceptable salt, ester or amide thereof.

10. A method of controlling undesirable vegetation which comprises contacting the vegetation or the locus thereof with or applying to the soil to prevent the emergence of vegetation an herbicidally effective amount of a 4-aminopicolinate of Formula I:

I

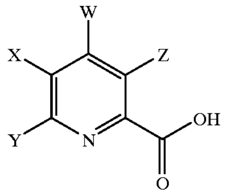

wherein

X represents H, halogen, $C_1$–$C_6$ alkoxy, $C_1$–$C_6$ alkylthio, aryloxy, nitro or trifluoromethyl;

Y represents halogen, $C_1$–$C_6$ alkoxy, $C_1$–$C_6$ alkylthio, aryloxy, heteroaryloxy or trifluoromethyl;

Z represents halogen, $C_1$–$C_6$ alkoxy, $C_1$–$C_6$ alkylthio, aryloxy or nitro; and W represents —$NO_2$, —$N_3$, —$NR_1R_2$, —N═$CR_3R_4$ or —NHN═$CR_3R_4$ where $R_1$ and $R_2$ independently represent H, $C_1$–$C_6$ alkyl, $C_3$–$C_6$ alkenyl, $C_3$–$C_6$ alkynyl, aryl, heteroaryl, hydroxy, $C_1$–$C_6$ alkoxy, amino, $C_1$–$C_6$ acyl, $C_1$–$C_6$ carboalkoxy, $C_1$–$C_6$ alkylcarbamyl, $C_1$–$C_6$ alkylsulfonyl, $C_1$–$C_6$ trialkylsilyl or $C_1$–$C_6$ dialkyl phosphonyl or $R_1$ and $R_2$ taken together with N represent a 5- or 6-membered saturated or unsaturated ring which may contain additional O, S or N heteroatoms; and $R_3$ and $R_4$ independently represent H, $C_3$–$C_6$ alkyl, $C_3$–$C_6$ alkenyl, $C_3$–$C_6$ alkynyl, aryl or heteroaryl or $R_3$ and $R_4$ taken together with ═C represent a 5- or 6-membered saturated ring; and agriculturally acceptable derivatives of the carboxylic acid, with the proviso that when X represents Cl, then Y and Z are not both Cl.

11. A method of claim 10 wherein:

X represents H, halogen or trifluoromethyl;

Y represents halogen, aryloxy, heteroaryloxy or trifluoromethyl;

Z represents halogen;

W represents —$NR_1R_2$ where $R_1$ and $R_2$ independently represent H, $C_1$–$C_6$ alkyl, $C_3$–$C_6$ alkenyl, $C_3$–$C_6$ alkynyl or $R_1$ and $R_2$ taken together with N represent a 5- or 6-membered saturated ring which may contain additional O or N heteroatoms; and agriculturally acceptable salts, esters or amides of the carboxylic acid.

12. A method of claim 10 wherein:

X represents H or F;

Y represents F, Cl, Br or aryloxy;

Z represents Cl; and

W represents —$NH_2$.

13. A method of claim 10 wherein:

Y represents a phenoxy group substituted with halogen or $C_1$–$C_4$ alkyl groups in the 3-position.

14. A method of claim 10 which comprises contacting the vegetation or the locus thereof with or applying to the soil to prevent the emergence of vegetation an herbicidally effective amount of 4-amino-3,6-dichloropyridine-2-carboxylic acid or an agriculturally acceptable salt, ester or amide thereof.

* * * * *

UNITED STATES PATENT AND TRADEMARK OFFICE
CERTIFICATE OF CORRECTION

PATENT NO. : 6,297,197 B1
DATED : October 2, 2001
INVENTOR(S) : Stephen Craig Fields et al.

It is certified that error appears in the above-identified patent and that said Letters Patent is hereby corrected as shown below:

Column 12,
Lines 22-23, should read -- 7. Preparation of Methyl, 4-Amino-6-bromo-3,5-difluoropyridine-2-carboxylate (Compound 16) -- rather than "7. Preparation of 4-Amino-3,5-difluoro-6-bromopyridine-2-carboxylic Acid (Compounds 16)"
Line 39, should read -- the solid (4-amino-6-bromo-3,5-difluoropyridine-2- -- rather than "the solid (4-amino-6-chloro-3,5-difluoropyridine-2-"

Column 14,
Line 53, should read -- phenylthiopyridine-2-carboxylic Acid (Compound 24) -- rather than "phenylthiopyridine-2-carboxylate (Compound 24)"

Column 20,
Line 18, should read -- trifluoromethylpyridine-2-carboxylic Acid (Compound 45) -- rather than "trifluoromethylpyridine-2-carboxylate (Compound 45)"
Lines 29-30, should read -- 26. Preparation of Methyl, 4-Amino-3-chloro-6-triluoromethylpyridine-2-carboxylate -- rather than "26. Preparation of 4-Amino-3-chloro-6-triluoromethylpyridine-2-carboxylic Acid"

Columns 25-26,
Table 1, #15, should read -- 15 O-Me -- rather than "15 OH"
Table 1, #16, should read -- 16 O-Me -- rather than "16 OH"
Table 1, #23, should read -- 23 OH $NH_2$ S-Me -- rather than "23 OH $NH_2$ S-Et"

Columns 27-28,
Table 1, #45, should read -- 45 OH -- rather than "45 O-Me"

UNITED STATES PATENT AND TRADEMARK OFFICE

CERTIFICATE OF CORRECTION

PATENT NO. : 6,297,197 B1 
DATED : October 2, 2001
INVENTOR(S) : Stephen Craig Fields et al.

It is certified that error appears in the above-identified patent and that said Letters Patent is hereby corrected as shown below:

Columns 31-32,
Table 6, #15, should read -- 15 O-Me -- rather than "15 OH"
Table 6, #16, should read -- 16 O-Me -- rather than "16 OH"
Table 6, #23, should read -- 23 OH $NH_2$ S-Me -- rather than "23 OH $NH_2$ S-Et"
Table 6, #45, should read -- 45 OH -- rather than "45 O-Me"

Signed and Sealed this

First Day of June, 2004

JON W. DUDAS
*Acting Director of the United States Patent and Trademark Office*